US012588918B2

(12) United States Patent
Wallace et al.

(10) Patent No.: US 12,588,918 B2
(45) Date of Patent: Mar. 31, 2026

(54) INVERTING CAPTURE APPARATUSES HAVING MATERIAL DEPOTS

(71) Applicant: STRYKER CORPORATION, Fremont, CA (US)

(72) Inventors: Michael P. Wallace, Fremont, CA (US); E. Skott Greenhalgh, Maple Grove, MN (US); Jayson Delos Santos, Alamo, CA (US)

(73) Assignee: STRYKER CORPORATION, Fremont, CA (US)

( * ) Notice: Subject to any disclaimer, the term of this patent is extended or adjusted under 35 U.S.C. 154(b) by 752 days.

(21) Appl. No.: 17/867,423

(22) Filed: Jul. 18, 2022

(65) Prior Publication Data

US 2022/0346815 A1     Nov. 3, 2022

Related U.S. Application Data

(63) Continuation of application No. PCT/US2020/014854, filed on Jan. 23, 2020.

(51) Int. Cl.
*A61B 17/22*     (2006.01)
*A61B 17/00*     (2006.01)

(52) U.S. Cl.
CPC ................... *A61B 17/22031* (2013.01); *A61B 2017/00292* (2013.01); *A61B 2217/007* (2013.01)

(58) Field of Classification Search
CPC .... A61B 17/22031; A61B 2017/00292; A61B 2217/007; A61B 17/221;
(Continued)

(56) References Cited

U.S. PATENT DOCUMENTS

| 1,001,033 A | 8/1911 | Hofmann |
| 1,001,626 A | 8/1911 | Dockery |

(Continued)

FOREIGN PATENT DOCUMENTS

| AU | 2015210338 A1 | 8/2015 |
| CA | 1132426 A | 9/1982 |

(Continued)

OTHER PUBLICATIONS

Becker et al.; A 3-year multi-institutional experience with the liposhaver; Archives of facial Plastic Surgery; 1(3); pp. 171-176; Jul. 1999.

(Continued)

*Primary Examiner* — Eduardo C Robert
(74) *Attorney, Agent, or Firm* — Seager, Tufte & Wickhem, LLP

(57) ABSTRACT

Inverting tube apparatuses and methods of using same for removing large amounts of material from a body lumen. The apparatuses and methods described herein may use a depot for holding, in a compressed configuration, a length of the flexible tube configured to invert over the distal end of an inversion support catheter to capture material within a body lumen. The depot is configured to facilitate the release of the flexible tube with a low release force, and in a manner that prevents snagging or binding of the flexible tube either on the body of the catheter or when rolling and inverting into the inversion support catheter.

20 Claims, 9 Drawing Sheets

(58) Field of Classification Search
CPC .... A61B 2017/2215; A61B 2017/3435; A61B
2017/22079; A61B 2017/22038; A61B
17/22; A61B 17/320725; A61B
2017/00398; A61B 2017/00778; A61B
2017/22034; A61B 17/32032; A61B
2017/00349; A61B 2017/306; A61B
2217/005; A61B 17/00234; A61B
2017/00867; A61B 17/32075; A61B
10/04; A61B 1/00151
See application file for complete search history.

(56) References Cited

U.S. PATENT DOCUMENTS

| | | | |
|---|---|---|---|
| 1,002,875 A | | 9/1911 | Schnoor |
| 1,013,038 A | | 12/1911 | Mitchell |
| 1,027,186 A | | 5/1912 | Dambach |
| 1,032,788 A | | 7/1912 | Slacinski |
| 3,515,137 A | | 6/1970 | Santomieri |
| 4,222,380 A | | 9/1980 | Terayama |
| 4,243,040 A | | 1/1981 | Beecher |
| 4,324,262 A | | 4/1982 | Hall |
| 4,469,100 A | * | 9/1984 | Hardwick ......... A61M 25/1002 |
| | | | 604/908 |
| 4,604,094 A | | 8/1986 | Shook |
| 4,646,736 A | | 3/1987 | Auth |
| 4,863,440 A | | 9/1989 | Chin |
| 4,946,440 A | | 8/1990 | Hall |
| 5,011,488 A | | 4/1991 | Ginsburg |
| 5,091,316 A | | 2/1992 | Monthony et al. |
| 5,236,423 A | * | 8/1993 | Mix ................... A61M 25/0111 |
| | | | 600/920 |
| 5,329,923 A | | 7/1994 | Lundquist |
| 5,364,345 A | | 11/1994 | Lowery et al. |
| 5,374,247 A | | 12/1994 | Lowery et al. |
| 5,389,100 A | | 2/1995 | Bacich et al. |
| 5,662,703 A | | 9/1997 | Yurek et al. |
| 5,908,435 A | | 6/1999 | Samuels |
| 5,971,938 A | | 10/1999 | Hart et al. |
| 6,156,055 A | | 12/2000 | Ravenscroft |
| 6,221,006 B1 | | 4/2001 | Dubrul et al. |
| 6,238,412 B1 | | 5/2001 | Dubrul et al. |
| 6,245,078 B1 | | 6/2001 | Ouchi |
| 6,258,115 B1 | | 7/2001 | Dubrul |
| 6,544,278 B1 | | 4/2003 | Vrba et al. |
| 6,569,181 B1 | | 5/2003 | Burns |
| 6,620,179 B2 | | 9/2003 | Boock et al. |
| 6,635,068 B1 | | 10/2003 | Dubrul et al. |
| 6,635,070 B2 | | 10/2003 | Leeflang et al. |
| 6,830,561 B2 | | 12/2004 | Jansen et al. |
| 6,846,029 B1 | | 1/2005 | Ragner et al. |
| 6,942,682 B2 | | 9/2005 | Vrba et al. |
| 7,621,870 B2 | | 11/2009 | Berrada et al. |
| 7,780,696 B2 | | 8/2010 | Daniel et al. |
| 8,057,496 B2 | | 11/2011 | Fischer, Jr. |
| 8,070,769 B2 | | 12/2011 | Broome |
| 8,092,486 B2 | | 1/2012 | Berrada et al. |
| 8,657,867 B2 | | 2/2014 | Dorn et al. |
| 8,721,714 B2 | | 5/2014 | Kelley |
| 8,784,442 B2 | | 7/2014 | Jones et al. |
| 8,795,305 B2 | | 8/2014 | Martin et al. |
| 8,956,384 B2 | | 2/2015 | Berrada et al. |
| 9,028,401 B1 | | 5/2015 | Bacich et al. |
| 9,125,683 B2 | | 9/2015 | Farhangnia et al. |
| 9,126,016 B2 | | 9/2015 | Fulton |
| 9,155,552 B2 | | 10/2015 | Ulm, III |
| 9,173,668 B2 | | 11/2015 | Ulm, III |
| 9,186,487 B2 | | 11/2015 | Dubrul et al. |
| 9,259,237 B2 | | 2/2016 | Quick et al. |
| 9,351,747 B2 | | 5/2016 | Kugler et al. |
| 9,358,037 B2 | | 6/2016 | Farhangnia et al. |
| 9,381,028 B2 | | 7/2016 | Smith |
| 9,427,244 B2 | | 8/2016 | Lund-Clausen et al. |
| 9,463,035 B1 | | 10/2016 | Greenhalgh et al. |
| 9,636,125 B2 | | 5/2017 | Sepetka et al. |
| 9,643,035 B2 | | 5/2017 | Mastenbroek |
| 9,717,514 B2 | | 8/2017 | Martin et al. |
| 9,848,975 B2 | | 12/2017 | Hauser |
| 9,849,014 B2 | | 12/2017 | Kusleika |
| 9,924,958 B2 | | 3/2018 | Martin et al. |
| 9,962,178 B2 | | 5/2018 | Greenhalgh et al. |
| 10,010,335 B2 | | 7/2018 | Greenhalgh et al. |
| 10,016,266 B2 | | 7/2018 | Hauser |
| 10,028,759 B2 | | 7/2018 | Wallace et al. |
| 10,130,385 B2 | | 11/2018 | Farhangnia et al. |
| 10,271,864 B2 | | 4/2019 | Greenhalgh et al. |
| 10,327,883 B2 | | 6/2019 | Yachia et al. |
| 10,512,478 B2 | | 12/2019 | Greenhalgh et al. |
| 10,517,624 B2 | | 12/2019 | Wallace et al. |
| 10,561,431 B2 | | 2/2020 | Greenhalgh et al. |
| 10,610,245 B2 | | 4/2020 | Wallace et al. |
| 10,779,843 B2 | | 9/2020 | Wallace et al. |
| 10,835,268 B2 | | 11/2020 | Wallace et al. |
| 10,835,269 B1 | | 11/2020 | Wallace et al. |
| 10,842,513 B2 | | 11/2020 | Greenhalgh et al. |
| 10,856,894 B2 | | 12/2020 | Wallace et al. |
| 10,863,999 B2 | | 12/2020 | Wallace et al. |
| 10,888,342 B2 | | 1/2021 | Wallace et al. |
| 10,888,343 B2 | | 1/2021 | Wallace et al. |
| 10,898,216 B2 | | 1/2021 | Lorenzo et al. |
| 10,912,576 B2 | | 2/2021 | Wallace et al. |
| 11,013,523 B2 | | 5/2021 | Arad Hadar |
| 11,026,709 B2 | | 6/2021 | Greenhalgh et al. |
| 11,103,265 B2 | | 8/2021 | Wallace et al. |
| 11,129,630 B2 | | 9/2021 | Skillrud et al. |
| 11,253,291 B2 | | 2/2022 | Wallace et al. |
| 11,266,414 B2 | | 3/2022 | Fulton, III |
| 11,298,145 B2 | | 4/2022 | Skillrud et al. |
| 11,471,176 B2 | | 10/2022 | Greenhalgh et al. |
| 11,497,512 B2 | | 11/2022 | Wallace et al. |
| 11,497,514 B2 | | 11/2022 | Greenhalgh et al. |
| 11,559,320 B2 | | 1/2023 | Wallace et al. |
| 11,627,973 B2 | | 4/2023 | Wallace et al. |
| 11,771,450 B2 | | 10/2023 | Wallace et al. |
| 11,812,980 B2 | | 11/2023 | Wallace et al. |
| 2001/0011182 A1 | | 8/2001 | Dubrul et al. |
| 2002/0032455 A1 | | 3/2002 | Boock et al. |
| 2002/0035373 A1 | | 3/2002 | Carlson et al. |
| 2002/0173819 A1 | | 11/2002 | Leeflang et al. |
| 2003/0040704 A1 | | 2/2003 | Dorros et al. |
| 2003/0083693 A1 | | 5/2003 | Daniel et al. |
| 2003/0114922 A1 | | 6/2003 | Iwasaka et al. |
| 2003/0135258 A1 | | 7/2003 | Andreas et al. |
| 2003/0153873 A1 | | 8/2003 | Luther et al. |
| 2003/0168068 A1 | * | 9/2003 | Poole ................. A61B 1/00156 |
| | | | 128/850 |
| 2003/0176884 A1 | | 9/2003 | Berrada et al. |
| 2003/0208223 A1 | * | 11/2003 | Kleiner .............. A61B 17/3431 |
| | | | 606/198 |
| 2003/0208224 A1 | | 11/2003 | Broome |
| 2004/0098033 A1 | | 5/2004 | Leeflang et al. |
| 2004/0153110 A1 | | 8/2004 | Kurz et al. |
| 2004/0199202 A1 | | 10/2004 | Dubrul et al. |
| 2005/0085826 A1 | | 4/2005 | Nair et al. |
| 2005/0085849 A1 | | 4/2005 | Sepetka et al. |
| 2005/0119668 A1 | | 6/2005 | Teague et al. |
| 2005/0177132 A1 | | 8/2005 | Lentz et al. |
| 2005/0187570 A1 | | 8/2005 | Nguyen et al. |
| 2005/0245876 A1 | | 11/2005 | Khosravi et al. |
| 2005/0283166 A1 | | 12/2005 | Greenhalgh |
| 2005/0283186 A1 | | 12/2005 | Berrada et al. |
| 2006/0042786 A1 | | 3/2006 | Chen |
| 2006/0047286 A1 | | 3/2006 | West |
| 2006/0089533 A1 | | 4/2006 | Ziegler et al. |
| 2006/0100662 A1 | | 5/2006 | Daniel et al. |
| 2006/0173525 A1 | | 8/2006 | Behl et al. |
| 2006/0195137 A1 | | 8/2006 | Sepetka et al. |
| 2006/0200221 A1 | | 9/2006 | Malewicz |
| 2006/0276874 A1 | | 12/2006 | Wilson et al. |
| 2006/0293696 A1 | | 12/2006 | Fahey et al. |
| 2007/0060839 A1 | | 3/2007 | Richardson |
| 2007/0112374 A1 | * | 5/2007 | Paul ........................ A61F 2/013 |
| | | | 606/200 |
| 2007/0123798 A1 | | 5/2007 | Rahamimov |

(56)                References Cited

U.S. PATENT DOCUMENTS

| | | |
|---|---|---|
| 2007/0149996 A1 | 6/2007 | Coughlin |
| 2007/0213765 A1 | 9/2007 | Adams et al. |
| 2008/0183136 A1 | 7/2008 | Lenker et al. |
| 2008/0183163 A1 | 7/2008 | Lampropoulos et al. |
| 2009/0018602 A1 | 1/2009 | Mitelberg et al. |
| 2009/0076417 A1 | 3/2009 | Jones |
| 2009/0270974 A1 | 10/2009 | Berez et al. |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desai et al. |
| 2010/0190156 A1 | 7/2010 | Van et al. |
| 2010/0249815 A1 | 9/2010 | Jantzen et al. |
| 2011/0034987 A1 | 2/2011 | Kennedy |
| 2011/0060359 A1 | 3/2011 | Hannes et al. |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0059309 A1 | 3/2012 | Di et al. |
| 2012/0059356 A1 | 3/2012 | Di Palma et al. |
| 2012/0083824 A1 | 4/2012 | Berrada et al. |
| 2012/0083868 A1 | 4/2012 | Shrivastava et al. |
| 2012/0165859 A1 | 6/2012 | Eckhouse et al. |
| 2012/0271105 A1 | 10/2012 | Nakamura et al. |
| 2013/0030461 A1 | 1/2013 | Marks et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0178888 A1 | 7/2013 | Bliss et al. |
| 2013/0226196 A1 | 8/2013 | Smith |
| 2013/0267870 A1 | 10/2013 | Lonky |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005717 A1 | 1/2014 | Martin et al. |
| 2014/0039398 A1* | 2/2014 | Rottenberg ....... A61M 25/0606 |
| | | 604/164.01 |
| 2014/0046133 A1 | 2/2014 | Nakamura et al. |
| 2014/0135814 A1 | 5/2014 | Sepetka et al. |
| 2014/0155980 A1 | 6/2014 | Turjman et al. |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0112376 A1 | 4/2015 | Molaei et al. |
| 2015/0133727 A1 | 5/2015 | Bacich et al. |
| 2015/0157303 A1 | 6/2015 | Brandeis |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0351775 A1 | 12/2015 | Fulton, III |
| 2015/0359547 A1 | 12/2015 | Vale et al. |
| 2016/0022293 A1 | 1/2016 | Dubrul et al. |
| 2016/0058458 A1 | 3/2016 | Hansen et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0183965 A1 | 6/2016 | Cully et al. |
| 2016/0206371 A1 | 7/2016 | Elgaard et al. |
| 2016/0228134 A1 | 8/2016 | Martin et al. |
| 2016/0242799 A1 | 8/2016 | Bonneau et al. |
| 2016/0256179 A1 | 9/2016 | Walish et al. |
| 2017/0035445 A1 | 2/2017 | Nguyen et al. |
| 2017/0042571 A1 | 2/2017 | Levi |
| 2017/0086851 A1 | 3/2017 | Wallace et al. |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0112513 A1 | 4/2017 | Marchand et al. |
| 2017/0119411 A1 | 5/2017 | Shah |
| 2017/0202574 A1 | 7/2017 | Franco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1* | 10/2017 | Wallace ............... A61B 17/221 |
| 2017/0348014 A1 | 12/2017 | Wallace et al. |
| 2018/0036028 A1 | 2/2018 | Krolik et al. |
| 2018/0042624 A1 | 2/2018 | Greenhalgh et al. |
| 2018/0042626 A1 | 2/2018 | Greenhalgh et al. |
| 2018/0049766 A1 | 2/2018 | Nolan et al. |
| 2018/0070968 A1 | 3/2018 | Wallace et al. |
| 2018/0236205 A1 | 8/2018 | Krautkremer et al. |
| 2018/0325534 A1 | 11/2018 | Skillrud et al. |
| 2018/0325535 A1 | 11/2018 | Skillrud et al. |
| 2018/0353161 A1 | 12/2018 | Magana et al. |
| 2019/0033614 A1 | 1/2019 | Jung et al. |
| 2019/0046219 A1 | 2/2019 | Marchand et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0133628 A1 | 5/2019 | Follmer et al. |
| 2019/0336148 A1 | 11/2019 | Greenhalgh et al. |
| 2019/0343538 A1 | 11/2019 | Wallace et al. |
| 2019/0351194 A1 | 11/2019 | Korkuch et al. |
| 2020/0078045 A1 | 3/2020 | Wallace et al. |
| 2020/0107842 A1 | 4/2020 | Greenhalgh et al. |
| 2020/0129194 A1 | 4/2020 | Wallace et al. |
| 2020/0178991 A1 | 6/2020 | Greenhalgh et al. |
| 2020/0178992 A1 | 6/2020 | Wallace et al. |
| 2020/0197032 A1 | 6/2020 | Wallace et al. |
| 2020/0281612 A1 | 9/2020 | Kelly et al. |
| 2020/0315642 A1 | 10/2020 | Greenhalgh et al. |
| 2020/0323520 A1 | 10/2020 | Greenhalgh et al. |
| 2021/0068854 A1 | 3/2021 | Wallace et al. |
| 2021/0069468 A1 | 3/2021 | Keating et al. |
| 2021/0106346 A1 | 4/2021 | Wallace et al. |
| 2021/0186543 A1 | 6/2021 | Wallace et al. |
| 2021/0353316 A1 | 11/2021 | Wallace et al. |
| 2022/0133348 A1 | 5/2022 | Wallace et al. |
| 2022/0322920 A1* | 10/2022 | Lewis ..................... A61B 1/05 |
| 2022/0346815 A1 | 11/2022 | Wallace et al. |
| 2022/0387053 A1 | 12/2022 | Wallace et al. |
| 2022/0401118 A1 | 12/2022 | Leguidleguid et al. |
| 2023/0069925 A1 | 3/2023 | Greenhalgh et al. |
| 2023/0076989 A1 | 3/2023 | Wallace et al. |
| 2023/0240695 A1 | 8/2023 | Wallace et al. |

FOREIGN PATENT DOCUMENTS

| | | |
|---|---|---|
| CN | 201079423 Y | 7/2008 |
| CN | 102186427 A | 9/2011 |
| CN | 102933161 A | 2/2013 |
| CN | 102988096 A | 3/2013 |
| CN | 202988096 U | 6/2013 |
| CN | 103764049 A | 4/2014 |
| CN | 103889347 A | 6/2014 |
| CN | 104000635 A | 8/2014 |
| CN | 104042304 A | 9/2014 |
| CN | 104068910 A | 10/2014 |
| CN | 104523320 A | 4/2015 |
| CN | 104582608 A | 4/2015 |
| CN | 108348319 A | 7/2018 |
| CN | 111281482 A | 6/2020 |
| CN | 112423683 A | 2/2021 |

(56) References Cited

FOREIGN PATENT DOCUMENTS

| CN | 112702961 A | 4/2021 |
| CN | 112969420 A | 6/2021 |
| CN | 109561903 B | 7/2021 |
| CN | 109310446 B | 8/2021 |
| CN | 109414272 B | 9/2021 |
| CN | 109561904 B | 9/2021 |
| CN | 113440223 A | 9/2021 |
| CN | 109890304 B | 11/2021 |
| CN | 113576607 A | 11/2021 |
| CN | 113876391 A | 1/2022 |
| CN | 109922744 B | 8/2022 |
| CN | 115697220 A | 2/2023 |
| CN | 110913778 B | 4/2023 |
| CN | 111343932 B | 5/2023 |
| EP | 1254634 A1 | 11/2002 |
| EP | 3509507 A1 | 7/2019 |
| EP | 3448276 B1 | 3/2020 |
| EP | 3448278 B1 | 5/2020 |
| EP | 3448280 B1 | 12/2020 |
| EP | 3590446 B1 | 1/2021 |
| EP | 3793457 A1 | 3/2021 |
| EP | 3849440 A1 | 7/2021 |
| EP | 3648686 B1 | 9/2021 |
| EP | 3849439 B1 | 1/2022 |
| EP | 3463114 B1 | 6/2022 |
| EP | 3448277 B1 | 7/2022 |
| EP | 3706650 B1 | 11/2022 |
| EP | 4091557 A1 | 11/2022 |
| EP | 4094699 A1 | 11/2022 |
| EP | 4103076 A1 | 12/2022 |
| EP | 4176830 A1 | 5/2023 |
| EP | 3984477 B1 | 7/2023 |
| EP | 4257064 A2 | 10/2023 |
| EP | 3939525 B1 | 12/2023 |
| GB | 1588072 A | 4/1981 |
| GB | 2498349 A | 7/2013 |
| JP | 2003-038500 A | 2/2003 |
| JP | 2003-135604 A | 5/2003 |
| JP | 2005-270464 A | 10/2005 |
| JP | 2016-041275 A | 3/2016 |
| JP | 2019-526381 A | 9/2019 |
| JP | 6873227 B2 | 5/2021 |
| JP | 6874120 B2 | 5/2021 |
| JP | 6924256 B2 | 8/2021 |
| JP | 2021-522952 A | 9/2021 |
| JP | 6934935 B2 | 9/2021 |
| JP | 6980703 B2 | 12/2021 |
| JP | 2022-500116 A | 1/2022 |
| JP | 2022-500120 A | 1/2022 |
| JP | 7170116 B2 | 11/2022 |
| JP | 7224308 B2 | 2/2023 |
| JP | 7239254 B2 | 3/2023 |
| JP | 7271535 B2 | 5/2023 |
| JP | 7271614 B2 | 5/2023 |
| WO | 00/32118 A1 | 6/2000 |
| WO | 02/02162 A2 | 1/2002 |
| WO | 2005/096963 A2 | 10/2005 |
| WO | 2008/088371 A2 | 7/2008 |
| WO | 2009/086482 A1 | 7/2009 |
| WO | 2012/009675 A2 | 1/2012 |
| WO | 2012/049652 A1 | 4/2012 |
| WO | 2012/162437 A1 | 11/2012 |
| WO | 2014/127738 A1 | 8/2014 |
| WO | 2015/189354 A1 | 12/2015 |
| WO | 2017/058280 A1 | 4/2017 |
| WO | 2017/189535 A2 | 11/2017 |
| WO | 2017/189550 A1 | 11/2017 |
| WO | 2017/189581 A1 | 11/2017 |
| WO | 2017/189591 A1 | 11/2017 |
| WO | 2017/189615 A1 | 11/2017 |
| WO | 2017/210487 A1 | 12/2017 |
| WO | 2018/049317 A1 | 3/2018 |
| WO | 2018/148174 A1 | 8/2018 |
| WO | 2019/010318 A1 | 1/2019 |
| WO | 2019/094456 A1 | 5/2019 |
| WO | 2019/222117 A1 | 11/2019 |
| WO | 2020/055866 A1 | 3/2020 |
| WO | 2020/055908 A1 | 3/2020 |
| WO | 2021/162678 A1 | 8/2021 |
| WO | 2021/167594 A1 | 8/2021 |

OTHER PUBLICATIONS

Wikipedia; Embolectomy; retrieved from the internet: https://en.wikipedia.org/wiki/Embolectomy;4 pgs.; retrieved/printed: Jan. 29, 2024.

PCT Invitation to Pay Additional Fees for International Appln. No. PCT/US2017/029345, mailed Oct. 17, 2017 [GWM-02 PCT1].

PCT International Search Report and Written Opinion for International Patent Appln. PCT/US2020/018655 dated Dec. 16, 2020; 22 pages.

EP Examination Report for EP Patent Appln. No. 18745794.0 dated Jul. 20, 2020; 4 pages.

European Patent Office Communication Rule 16.1(1) and 162 for EP Patent Appln. No. 17722277.5 dated Dec. 13, 2018; 3 pages [GWM-02 PCT2 EP1].

European Patent Office Communication Rule 161(1) and 162 EPC for EP Patent Appln. No. 17737084.8 dated Dec. 18, 2018; 3 pages [GWM-02 PCT1 EP1].

European Patent Office Communication Rule 161(1) and 162 for EP Patent Appln. No. 17721036.6 dated Dec. 13, 2018; 3 pages [GWM-02 PCT4 EP1].

European Patent Office Communication Rule 161(1) and 162 for EP Patent Appln. No. 17729703.3 dated Feb. 5, 2019; 3 pages [GWM-02 PCT5 EP1].

European Patent Office Communication Rule 161(1) and 162 for EP Patent Appln. No. 17772186.7 dated Apr. 23, 2019; 3 pages [GWM-02 PCT6 EP1].

European Patent Office Communication Rule161(1) and 162 for EP Patent Appln. No. 17722290.8 dated Dec. 13, 2018; 3 pages [GWM-02 PCT3 EP1].

European Search Report for European Patent Application No. 17729703.3 dated Oct. 7, 2019; 5 pages [GWM-02-PCT5 EP1].

PCT International Search Report and Written Opinion for International Patent Application No. PCT/US2019/050467 dated Dec. 18, 2019; 17 pages (GWM-07 PCT).

Extended European Search Report for EP Patent Application No. 22162955.3 dated Sep. 5, 2022.

Extended European Search Report for EP Patent Appln. No. 21192438.6 dated Nov. 23, 2021; 6 pages [GWM-03-EP2].

Extended European Search Report for European Patent Application No. 19191925.7 dated Oct. 8, 2019; 7 pages [GWM-02-PCT1 EP2].

Extended European Search Report for European patent Appln. No. 20185092.2; dated Sep. 11, 2020; 7 pages.

Extended European Search Report for European patent Appln. No. 16852212.6; dated Aug. 22, 2018; 6 pages [GWM-01 EP1].

Extended European Search Report for European patent Appln. No. 18174891.4 dated Oct. 5, 2018; 6 pages [GWM-01 EP2].

Foreign Communication Pursuant to Article 94(3) for EP Patent Appln. No. 17772186.7 dated Jun. 17, 2022 [GWM-02-PCT6EP1].

Foreign Communication Under Rule 71(3) for EP Patent Appln. No. 18807524.6 dated Jul. 1, 2022 [GWM-04 EP1].

Foreign Exam Report for EP Application No. 19773654.9 dated Aug. 24, 2021; 5 pages [GWM-08 EP1].

Foreign OA for EP Patent Applicaiton No. 19726855.0 dated May 18, 2022.

International Search Report and Written Opinion dated Feb. 28, 2018 for PCT/US2017/029345, American Stryker Corporation 26 pages.

International Search Report and Written Opinion for International Patent Appln. No. PCT/US2019/050410 dated Oct. 25, 2019.

International Search Report and Written Opinion for PCT/US16/017982 dated May 6, 2016; 18 pages [GWM-01 PCT].

PCT International Search Report and Written Opinion for International Patent Appln. PCT/US2020/017684 dated Nov. 30, 2020; 19 pages.

(56)                References Cited

OTHER PUBLICATIONS

International search report and written opinion for PCT/US2018/040937 dated Nov. 14, 2018; 16 pages [GWM-03 PCT].

International Search Report and Written Opinion for PCT/US2018/059607 dated Mar. 28, 2019; 24 pages [GWM-04 PCT].

Invitation to Pay Additional Fees for International Patent Appln. No. PCT/US2018/040937 dated Sep. 26, 2018; 11 pages [GWM-03 PCT].

Invitation to Pay Additional Fees for International Patent Appln. No. PCT/US2018/059607 dated Jan. 31, 2019; 16 pages [GWM-04 PCT].

Invitation to Pay Additional Fees for International Patent Appln. No. PCT/US2019/050467 dated Oct. 25, 2019; 12 pages [GWM-07 PCT].

Merriam Webster Dictionary; Jam; 15 pages; retrieved from the internet (https://www.merriam-webster.com/dictionary/jam) on Jan. 30, 2024.

O'Sullivan; Thrombolysis versus thrombectomy in acute deep vein thrombosis; Interventional Cardiology; 3(5); pp. 589-596; Oct. 2011.

PCT International Search Report and Written Opinion for International Appl. No. PCT/US2020/014854, dated Oct. 5, 2020 (13 pages).

PCT International Search Report and Written Opinion for International Appln. No. PCT/US2017/050933, dated Nov. 10, 2017; 14 pages [GWM-02 PCT6].

PCT International Search Report and Written Opinion for International Appln. No. PCT/US2017/029366, dated Aug. 29, 2017; 17 pages [GWM-02 PCT2].

PCT International Search Report and Written Opinion for International Appln. No. PCT/US2017/029440, dated Jul. 7, 2017; 15 pages [GWM-02 PCT3].

PCT International Search Report and Written Opinion for International Appln. No. PCT/US2017/029472, dated Jul. 7, 2017; 16 pages [GWM-02 PCT4].

PCT International Search Report and Written Opinion for International Appln. No. PCT/US2017/035543, dated Aug. 14, 2017; 12 pages [GWM-02 PCT5].

PCT International Search Report and Written Opinion for International Patent Appln. No. PCT/US2019/032061, Applicant Stryker Corporation, dated Jul. 23, 2019 (12 pages).

Extended European Search Report for European Patent Application No. 17729703.3 dated Oct. 7, 2019; 3.

* cited by examiner

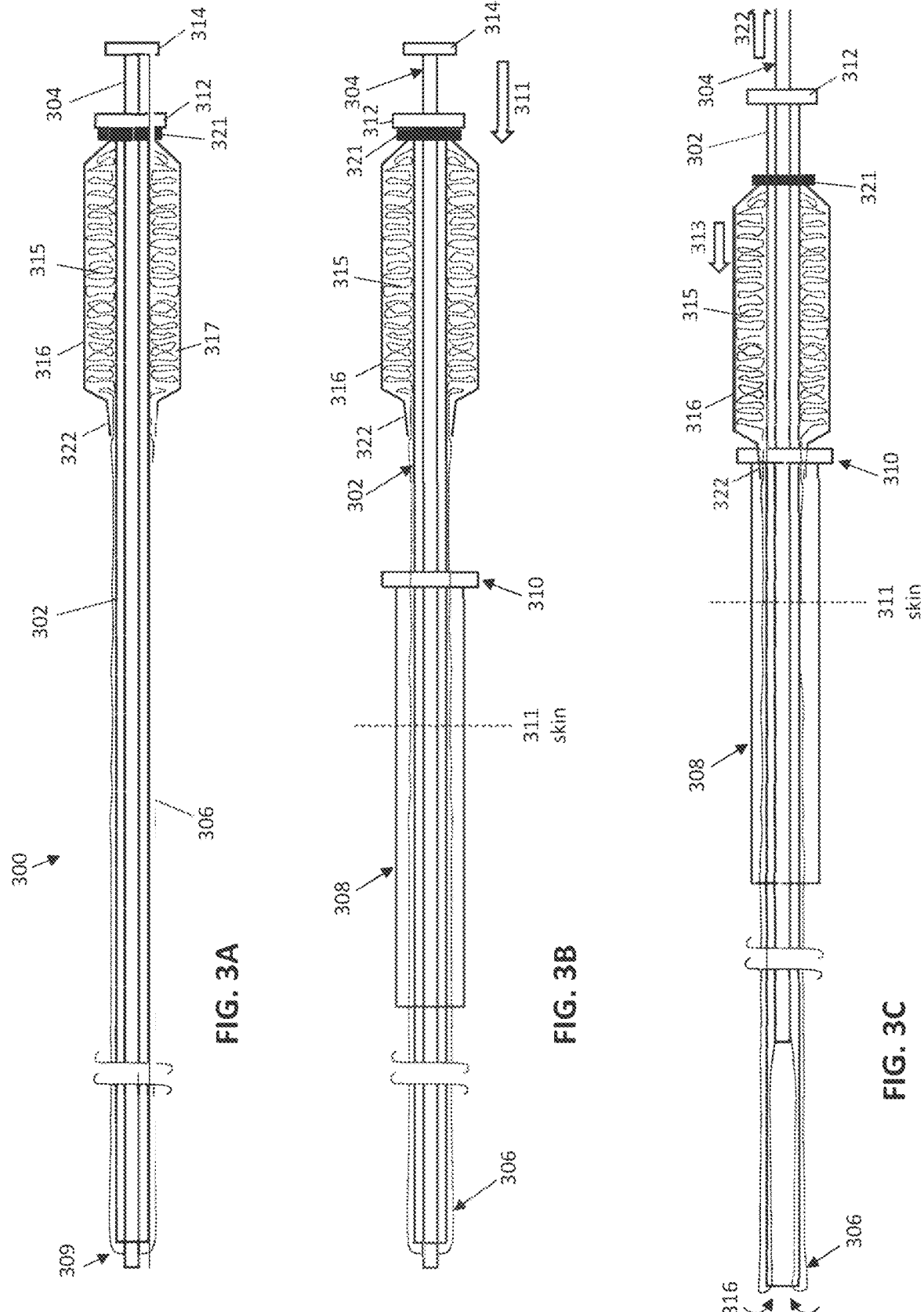

INVERTING CAPTURE APPARATUSES HAVING MATERIAL DEPOTS

CROSS REFERENCE TO RELATED APPLICATIONS

This patent application is a continuation of International Application No. PCT/US2020/014854, filed Jan. 23, 2020, which is related to U.S. patent application Ser. No. 16/397,089, filed Apr. 29, 2019, which is a continuation of U.S. patent application Ser. No. 15/291,015, filed Oct. 11, 2016, now U.S. Pat. No. 10,271,864, which is a continuation of U.S. patent application Ser. No. 15/043,996, filed on Feb. 15, 2016, now U.S. Pat. No. 9,463,035, which claims priority to each of U.S. provisional patent application nos. 62/284,300, filed Sep. 28, 2015, 62/284,752, filed Oct. 8, 2015, and 62/245,560, filed Oct. 23, 2015.

INCORPORATION BY REFERENCE

All U.S. patents and publications mentioned in this specification are incorporated by reference herein in their entirety to the same extent as if each individual patent or publication was specifically and individually indicated to be incorporated by reference.

FIELD

The apparatuses and methods described herein relate to mechanical removal of material from within a body lumen. In particular, described herein are mechanical inverting tube apparatuses having a depot configured to hold the flexible tube in a quick-release configuration.

BACKGROUND

It is often necessary to remove material from within a body lumen. For example, many vascular problems stem from insufficient blood flow through blood vessels, often caused by a blockage within the vessel referred to as a blood clot, or thrombus. Thrombi can occur for many reasons, including after a trauma such as surgery, or due to other causes. More than 1.2 million heart attacks in the United States are caused by blood clots (thrombi) which form within a coronary artery. It is often desirable to remove tissue from the body in a minimally invasive manner as possible, so as not to damage other tissues. For example, removal of tissue, such as blood clots, from within a patient's vasculature may improve patient conditions and quality of life.

Mechanical inverting tube apparatuses (e.g., including, but not limited to, mechanical thrombectomy devices) may be particularly advantageous. There is a definite need for thrombectomy devices, and particularly for mechanical thrombectomy devices that can be easily and accurately delivered through the, often tortious, anatomy in the peripheral and central vasculature, then be reliably deployed to remove clot material. In particular, there is a need for mechanical inverting tube apparatuses that are easy to operate and that are capable of removing large volumes of material from a body lumen (e.g., a blood vessel) using an inverting tube without requiring reloading of the inverting tube Described herein are apparatuses and methods that may address these needs.

SUMMARY OF THE DISCLOSURE

Described herein are apparatuses and methods using and making such apparatuses for removing material from a body lumen and methods of using them. In particular, these apparatuses (e.g., devices, systems, etc.) and methods of using and making them may be used to remove large amounts of material from the body lumen. The apparatuses typically operate by inverting a flexible tube, e.g., a knitted, woven, braided, solid, or laser-cut tube, over a distal end opening of a catheter so that the flexible tube rolls into the catheter and draws material from the body lumen with it into the catheter. These apparatuses, which may be referred to herein as inverting tube apparatuses, may operate continuously within a body until the entire length of flexible tube has been drawn into the catheter, after which point the apparatus must be withdrawn and removed. The apparatuses and methods described herein are adapted to include a depot for holding, in a compressed configuration, a long length of the flexible tube. The depot is preferably configured to facilitate the release of the flexible tube with a low release force, and in a manner that prevents snagging or binding of the flexible tube on the body of the catheter or when rolling and inverting into the catheter.

The inverting tube apparatuses described herein are particularly useful for removing clots (e.g., thrombi) from blood vessels. In some variations these apparatuses may be referred to as inverting mechanical thrombectomy apparatuses and/or inverting tube thrombectomy apparatuses. These apparatuses may be deployed to efficiently ingest one or more large clots, without requiring reloading or replacement. For example, the apparatuses described herein may be configured to provide a high pulling efficiency (e.g., low resistance) to ingest and remove clots including relatively long clots (e.g., greater than 10 mm length, greater than 15 cm, greater than 20 cm, greater than 25 cm, greater than 30 cm, greater than 35 cm, etc.). As such, the apparatuses described herein may be configured to store long lengths of flexible tube at a proximal end of the apparatus, thereby enabling removal of large volumes of clot in a single pass. The apparatuses described herein may include one or more features that allow even longer flexible tubes, such as flexible tubes that are longer than the length of the catheter (e.g., the inversion support catheter) over which the flexible tube is being inverted, to be withdrawn easily, without jamming or binding on the catheter.

In general, the apparatuses described herein for removing material from a body lumen include an elongate inversion support catheter having a proximal end region, a distal end region, and a distal end opening, and a flexible tube having a distal first end that may be pulled proximally through the catheter, and a depot on the proximal end region of the support catheter holding some of the flexible tube in a compressed configuration. The flexible tube may extend over an outer surface of the inversion support catheter be configured to invert into the distal end opening of the inversion support catheter when pulled proximally through the inversion support catheter. The depot on the proximal end region of the inversion support catheter include an inner storage region configured such that a proximal portion of the flexible tube may be held in a compressed configuration within the inner storage region, wherein the proximal portion of the flexible tube is configured to unfurl out of a distal end opening of the depot when the flexible tube pulled proximally into the inversion support catheter.

In one exemplary embodiment, an apparatus for removing material from a body lumen includes: an elongate inversion support catheter having a proximal end region, a distal end region, and a distal end opening; an elongate puller extending within the inversion support catheter; a flexible tube having a distal first end attached to the puller, wherein the flexible tube extends over an outer surface of the inversion support catheter and is configured to invert into the distal end opening of the inversion support catheter when the puller is pulled proximally; a depot on the proximal end region of the inversion support catheter, the depot comprising an inner storage region, wherein a proximal portion of the flexible tube is held compressed within the inner storage region in a folded pattern (e.g., scrunched up along the elongate length, forming a zig-zag pattern) and is configured to unfurl out of a distal end opening of the depot when the puller is pulled proximally; and a distal guide forming the distal end opening of the depot, wherein the distal guide is configured to engage with a sheath and to guide the flexible tube out of the depot as the flexible tube is unfurled.

Any of the apparatuses described herein may optionally include a puller disposed within the inversion support catheter to which the first end of the flexible tube is connected, e.g., at or near the distal end region of the puller. The puller may (at least initially) reside within the inversion support catheter, and may be pulled proximally to invert and roll the flexible tube into the inversion support catheter. In some variations, the flexible tube may be sufficiently long such that, even after the puller is completely withdrawn from the lumen of the inversion support catheter, the medical practitioner performing the clot removal procedure may continue to pull on the flexible tube to remove additional material from the body lumen.

In various embodiments, the flexible tube may be formed of any material, and particularly knitted, woven, braided or slotted materials, including knitted, woven and/or braided materials formed of a fiber (e.g., metallic, polymeric, etc., such as Nitinol, stainless steel, etc.). The flexible tube may be shape-set. In some variations the flexible tube may be formed to a shape having an inner diameter (ID) in the un-inverted configuration (e.g., that rides over the outside surface of the inversion support catheter) that is slightly larger than the outer diameter (OD) of the catheter. In general, these apparatuses may be delivered into the body within an intermediate catheter (sometime referred to herein as a delivery catheter). In some variations the flexible tube may have a maximum outer diameter in the un-inverted configuration that is the same or slightly smaller than the inner diameter of the intermediate catheter. Configuring the outer diameter of the flexible tube to be between the ID of the intermediate catheter and the OD of the inversion support catheter may reduce the pull force needed to withdraw the flexible tube into the inversion support catheter. This may be particularly useful for inversion support catheters that are longer than, for example, about 15 cm (e.g., about 40 cm or longer, about 50 cm or longer, about 60 com or longer, about 90 cm or longer, etc.). In some variations, the flexible tube may be compressed within the depot in a folded, zig-zag (e.g., "scrunched" up) configuration, so that the diameter may vary, allowing five-fold or greater (e.g., ten-fold or more, 15 fold or more, 20 fold or more, 25 fold or more, etc.) compression within the depot.

In another exemplary embodiment, an apparatus for removing a material from a body lumen includes: an elongate inversion support catheter having a proximal end region, a distal end region, and a distal end opening; an elongate puller extending within the inversion support catheter; a flexible tube having a distal first end attached to the puller, wherein the flexible tube extends over an outer surface of the inversion support catheter and is configured to invert into the distal end opening of the inversion support catheter when the puller is pulled proximally; and a depot on the proximal end region of the inversion support catheter, the depot comprising an inner storage region, wherein a proximal portion of the flexible tube is held compressed within the inner storage region in a folded, e.g., fan-folded and/or zig-zag pattern, and is configured to unfurl out of a distal end opening of the depot when the puller is pulled proximally.

Any of these apparatuses may further include a distal guide forming the distal end opening of the depot, wherein the distal guide is configured to guide the flexible tube out of the depot as the flexible tube is unfurled. For example, the distal guide may present a lubricious surface (e.g., including a liner and/or coated by and/or formed of a material that is itself lubricious such as PTFE, PE, etc. Thus, the distal guide may comprise a lubricious material. The distal guide may be configured to form an annular channel out of which the compressed flexible tube may leave the inner storage region of the depot. In some variations, the distal guide is configured to engage with an introducer sheath to secure the depot to the introducer sheath. Coupling the depot (e.g., the distal guide portion of the depot) to the introducer sheath may advantageously stabilize the depot (and therefore the flexible tube) as the device is advanced and/or actuated. In general, the depot, and in particular the distal guide portion of the depot when included, may be configured to engage over a proximal sheath hub of the introducer sheath. In alternative embodiments, the depot is instead configured to engage within a proximal sheath hub of the introducer sheath.

The distal guide portion of the depot may extend nearly completely or partially along the length of the inversion support catheter. The distal guide may extend greater than 40% (e.g., greater than 45%, greater than 50%, greater than 55%, greater than 60%, greater than 65%, greater than 70%, greater than 75%, greater than 80%, etc.) of the length of the inversion support catheter. For example, the distal guide may extend distally over the outer surface of the inversion support catheter for greater than 5 cm (e.g., greater than 10 cm, greater than 15 cm, greater than 20 cm, greater than 25 cm, greater than 30 cm, greater than 35 cm, greater than 40 cm, greater than 45 cm, etc.). In some variations, the depot is configured so that the user may be able to see into the inner storage region of the depot. For example, the depot may comprise a transparent outer region allowing visualization of the flexible tube within the inner storage region. In some variations the depot includes a window or port for viewing the inner storage region.

As mentioned above, the flexible tube may be compressed within the inner storage region into a folded configuration (e.g., fanfold and/or zig-zag pattern), in which the flexible tube forms alternating right and left turns. As used herein the folded configuration is approximate, in that the turns (e.g., folds) may be non-uniformly arranged and may be irregular in size and shape. In some variations the folding is a scrunching along the length of the tube (e.g., over a mandrel and/or the inversion support catheter). The fold may be referred to as a fanfold, with repeated folds along the tube length. The bends forming the folds (fanfolds) may be 'soft' (e.g., curves) rather than sharp (e.g., angular) or a combination of both. The fanfold pattern may also be referred to herein as a zig-zag pattern. Examples of this scrunched-up pattern are provided herein, in which the flexible tube may stack up along the longitudinal length, compressing the flexible tube. In some variations the folded flexible tube may form regions of larger and smaller outer diameter (OD).

In some variations, the OD may be approximately the same, but the flexible tube maybe compressed in a pattern, such as a helical pattern, around the portion of the inversion support catheter within the depot (e.g., within the inner storage region of the depot). In some variations the folded (e.g., zig-zag pattern) of the flexible tube is arranged approximately in parallel to a long axis of the inversion support catheter. Alternatively, the folded (e.g., zig-zag) pattern of the flexible tube may be arranged approximately transverse to a long axis of the inversion support catheter. The flexible tube may be shape-set into the compressed (e.g., zig-zag, the "scrunched" pattern, etc.). In some variations the flexible tube is instead shape set into the un-compressed (e.g., elongated) form.

The apparatuses described herein may be configured to store a majority (i.e., greater than 50%) of the flexible tube in a compressed, primed to release configuration within the depot. For example, in some variations greater than 50% of the length of the flexible tube (e.g., greater than 55%, greater than 60%, greater than 65%, greater than 70%, greater than 75%, etc.) is held within the depot in an undeployed configuration.

In some variations, the flexible tube may be held compressed within the inner storage region with three fold or greater (e.g., 5 fold or greater, 7 fold or greater, 10 fold or greater, 12 fold or greater, 15 fold or greater, 17 fold or greater, 20 fold or greater, etc.) compression along the length of the flexible tube. Any of the apparatuses described herein may further include an introducer sheath; wherein the depot may be configured to engage with the introducer sheath, as described above. In some variations, the depot may include one or more valves configured to receive a flushing solution and/or a pressurizing solution.

Any of the depots may be configured to reduce the friction between the flexible tube and the depot and/or the inversion support catheter. For example, the depot may include an inner liner between the inner storage region and the inversion support catheter. In some variations, the inner store region is lubricious.

In general, the depot is slideably arranged on the inversion support catheter. In some variation the depot may be lockable to either or both the inversion support catheter (e.g., at a proximal end of the depot) and/or an introducer sheath. For example, the depot may be locked to the introducer sheath to secure it in position. Alternatively, or additionally, a proximal end of the depot may be configured to lock onto the proximal end region of the inversion support catheter.

Any appropriate flexible tube may be used. For example, in some variations, the flexible tube may be one of: a knit tube, a woven tube, a braided tube, a solid tube, or a laser-slotted tube.

Also described herein are methods for using any of the apparatuses described herein to remove a material, including (but not limited to a clot) from within a body lumen such as a vessel. For example a method of removing a clot from a blood vessel may include: advancing an inverting tube apparatus through the blood vessel until a distal end portion of the inverting tube apparatus is located proximate to the clot, wherein the inverting tube apparatus comprises an inversion support catheter having an elongate and flexible catheter body, a puller within a lumen of the inversion support catheter, and a flexible tube coupled at a distal end to the puller, the flexible tube extending over an exterior surface of the inversion support catheter, wherein the flexible tube is held compressed within an inner storage region of a depot on a proximal end region of the inversion support catheter; pulling the puller proximally to thereby roll the flexible tube over a distal end opening of the inversion support catheter so that the flexible tube captures the clot and pulls the clot proximally into the lumen of the inversion support catheter; wherein pulling the puller proximally draws the flexible tube from out of the depot so that the flexible tube unfurls distally from a compressed folded configuration (e.g., zig-zag pattern) within the depot.

Pulling the puller proximally to draw the flexible tube from out of the depot may include guiding the flexible tube out of the inner storage region using a distal guide on the depot. Any of these methods may also include inserting the inverting tube apparatus into an introducer sheath and into the blood vessel.

In some variations, the method of operation of the apparatus may include locking the depot to a proximal end of the introducer sheath. In some variations, the method may further include applying a pressure or force within the depot that may assist in expelling the flexible tube from the compressed configuration within the depot. For example, the method may further include pressurizing the inner storage region of the depot. In some variations, the method may further include injecting a lubricious material into the depot. In some variations, the method may further include injecting a contrast agent into the depot (in some variations the contrast agent may be pressurized and/or may be lubricious). Any of these materials may be injected through a flushing or pressurizing port. Any of these methods may further include flushing a flushing fluid through the depot.

BRIEF DESCRIPTION OF THE DRAWINGS

A better understanding of the features and advantages of the disclosed apparatuses and methods of using same will be obtained by reference to the following detailed description when read in conjunction with reviewing the accompanying drawings, in which:

In FIG. 1A, the assembled apparatus is shown in a side view, showing an inversion support catheter and a flexible outer tube. FIG. 1B shows the inverting tube apparatus of FIG. 1A in a vessel, proximal to a clot. FIG. 1C illustrates the removal of a clot from the vessel using the apparatus of FIG. 1A, by pulling the flexible tube on the outside of the inversion support catheter proximally so that it rolls over the distal end of the inversion support catheter and into the inversion support catheter, drawing the clot with it; the apparatus may be advanced distally.

FIGS. 3A-3C illustrate one example of a mechanical inverting tube apparatus having a proximal depot configured to hold the flexible tube in a quick-release configuration. FIG. 3A show the mechanical inverting tube apparatus including a proximal depot coupled to the inversion support catheter and housing the flexible tube. FIG. 3B shows the apparatus of FIG. 3A inserted through a sheath into a body lumen. FIG. 3C illustrates operation of the apparatus of FIG. 3A with the flexible tube being pulled proximally and inverting into the inversion support catheter to remove material from the vessel.

FIG. 4A shows the apparatus, including a distal funnel region. FIG. 4B illustrates the apparatus of FIG. 4A deployed into a body lumen (e.g., blood vessel).

DETAILED DESCRIPTION

In general, described herein are mechanical inverting tube apparatuses (e.g., systems and devices, including thrombectomy systems and thrombectomy devices) and methods of using them for removing material, such as thrombus (e.g., clot) material from a body lumen, such as a blood vessel. In particular, described herein are mechanical inverting tube apparatuses that include a depot configured to hold the flexible tube in a quick-release configuration. These apparatuses may be used to remove a larger amount of material, such as clot material, from a body lumen using an inverting flexible tube that may be many times longer than the length of the apparatus (e.g., the inversion support catheter) without jamming. The methods and apparatuses described herein represent a substantial improvement over previously described apparatuses that were either limited to a relatively small maximum length of flexible tube that could be used to invert and withdraw material, or were prone to jamming and failure within the body.

Figures 1A, 1B, 1C:
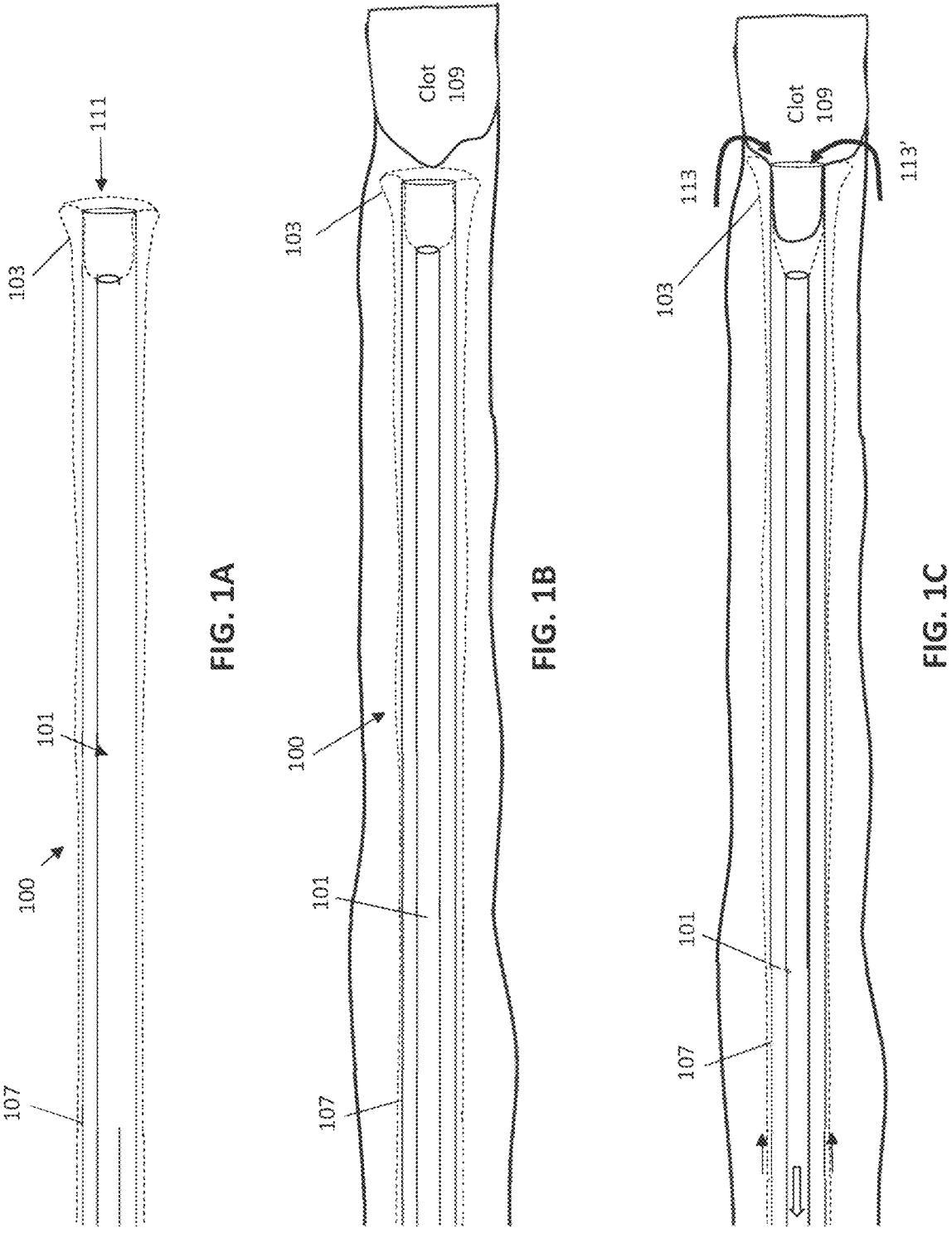
FIGS. 1A-1C illustrate an example of a mechanical inverting tube apparatus that may be used to remove material from a vessel.

In general, a mechanical inverting tube apparatus (also referred to as "mechanical thrombectomy apparatus" in some variations) may be configured to remove clot using a length of inverting tube, as shown in FIGS. 1A-1C. The apparatuses and methods of using them described herein may be effective for use with the vasculature, including the neurovasculature and the peripheral vasculature, including for use with relatively larger and/or longer clots (e.g., relative to the length of the flexible tube).

For example, FIG. 1A illustrates an example of an inverting tractor mechanical thrombectomy apparatus 100, such as described in U.S. patent application Ser. No. 15/496,570, and in U.S. Pat. No. 9,463,035. The apparatus includes an inversion support catheter 107 and a flexible tube 103 that extends over the outer surface of the inversion catheter. The flexible tube may be referred to as a tractor tube (or flexible tractor tube), and may be attached at one end region to a puller 101, which may be pull wire or pull tube (e.g., catheter), e.g., at the distal end region of the puller. In some variations the flexible tube may be attached proximal to the distal end of the puller (e.g. between 1 mm and 50 mm from the distal end, between 1 mm and 40 mm, between I mm and 30 mm, greater than 5 mm, greater than 10 mm, greater than 20 mm, greater than 30 mm, etc. from the distal end of the puller). Pulling the puller proximally inverts the flexible tube over the distal end opening 111 of the inversion support catheter to capture and remove a material (such as a clot) in the vessel lumen, as shown in FIGS. 1B and 1C. In operation, the amount of the material that may be captured corresponds to the length of the flexible tube.

In FIG. 1B the inverting tractor mechanical thrombectomy apparatus 100 is shown deployed near a clot 109. In the deployed configuration the puller 101 (shown here as a puller micro catheter, alternatively the puller may be a wire) is held within an elongate inversion support catheter 107 so that the flexile tractor tube 103 extends from the end of the puller 101 and expands toward the inner radius of the elongate inversion support catheter I 07; at the distal end opening 111 of the elongate inversion support catheter the tractor tube inverts over itself and extends proximally in an inverted configuration over the distal end of the elongate inversion support catheter. As shown in FIG. 1C, by pulling the puller proximally, the tractor tube rolls 113, 113' and everts over the distal end opening of the elongate inversion support catheter, drawing the adjacent clot into the elongate inversion support catheter, as shown.

FIG. 1A the elongate inversion support catheter is an elongate tube having a distal end that has the same size inner diameter as the proximal length of the inversion support catheter. In some variations the distal end of the inversion support catheter may be funnel-shaped (or configured to expand into a funnel shape, see, e.g. FIGS. 4A-4B). In FIGS. 1A-1C, the inversion support catheter 107 is shown positioned between the tractor tube (e.g., flexible tube 103) and the puller 101 so that the flexible tube can be pulled proximally by pulling on the puller and rolling the flexible tube into the elongate inversion support catheter so that it inverts. The portion of the flexible tube that is inverted over the distal end of the elongate inversion support catheter has an outer diameter that is greater than the outer diameter of the elongate inversion support catheter. The flexible tube may be biased so that it has a relaxed expanded configuration with a diameter that is greater than the outer diameter (OD) of the elongate inversion support catheter; in addition, the flexible tube may also be configured (e.g., by heat setting, etc.) so that when the flexible tube is everted and rolled over the distal end opening into the elongate inversion support catheter, the outer diameter of the flexible tube within the elongate inversion support catheter has an outer diameter that is about y times (y fold) the inner diameter of the elongate inversion support catheter (e.g., where y is greater than $0.1 \times$, $0.5 \times$, $0.6 \times$, $0.7 \times$, $0.75 \times$, $0.8 \times$, $0.9 \times$, $1 \times$, etc. the inner diameter, ID, of the elongate inversion support catheter. This combination of an un-inverted diameter of the flexible tube of greater than the diameter of the OD of the elongate inversion support catheter and an inverted diameter of the flexible tube of greater than, e.g., $0.7 \times$ the ID of the elongate inversion support catheter is surprisingly helpful for preventing jamming of the apparatus, both when deploying the apparatus and when rolling the flexible tube over the distal end opening of the elongate inversion support catheter to grab a clot. The flexible tube may be expandable and may be coupled to the puller as shown. In some variations the flexible tube and the puller may comprise the same material but the flexible tube may be more flexible and/or expandable, or may be connected to elongate puller (e.g., a push/pull wire or catheter). As mentioned above, the puller may be optional (e.g., the flexible tube may itself be pulled proximally into the inversion support catheter).

In FIG. 1C the clot may be drawn into the elongate inversion support catheter by pulling the flexible tube proximally into the distal end of the elongate inversion support catheter, as indicated by the arrows 113, 113' showing pulling of the inner portion of the flexible tube, resulting in rolling the flexible tube over the end opening of the catheter and into the catheter distal end and inverting the expandable distal end region so that it is pulled into the catheter, shown by arrows. The end of the flexible tube outside of the catheter may be loose relative to the outer wall of the catheter.

Figures 2A, 2B, 2C:
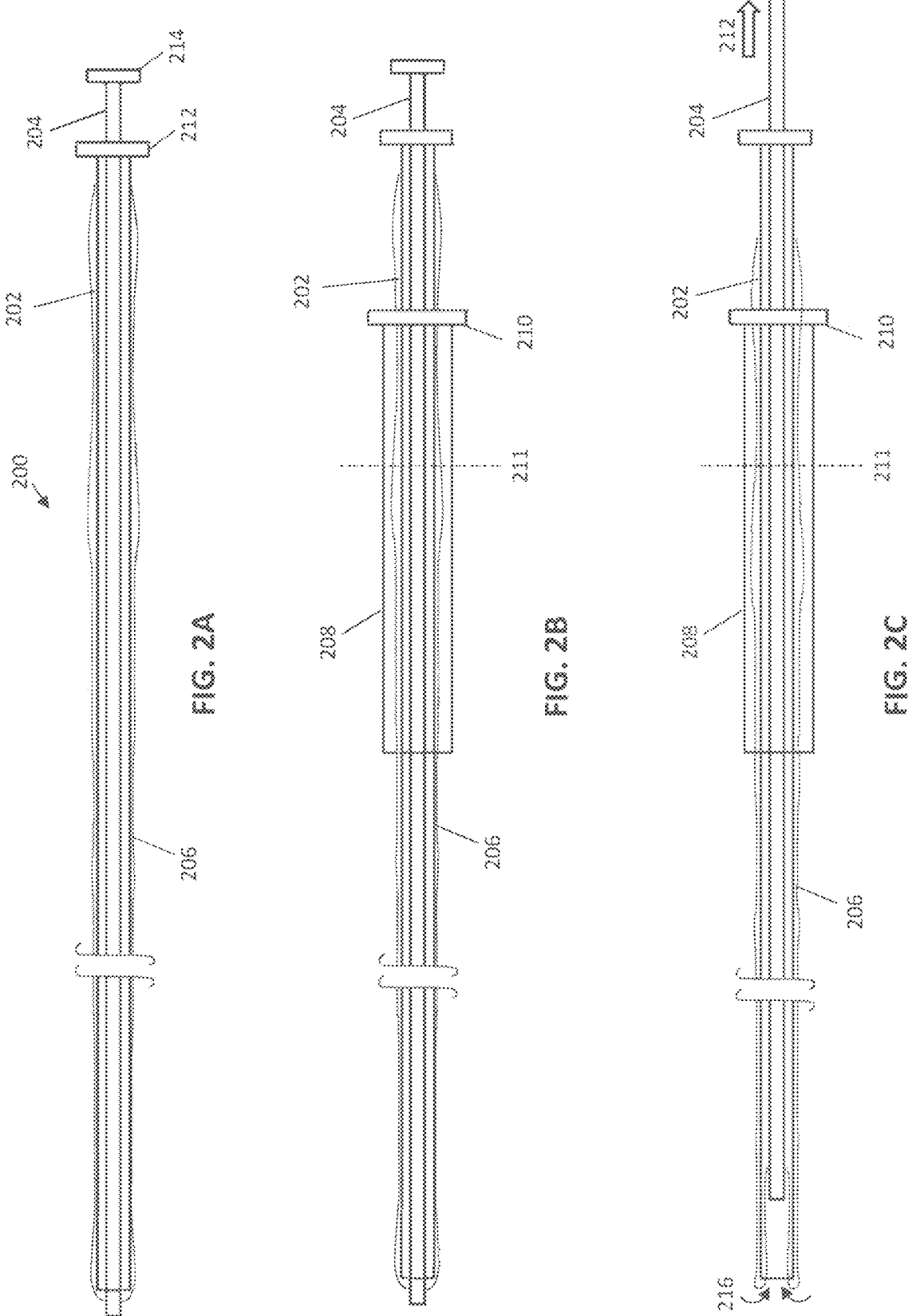
FIG. 2A is an example of a mechanical inverting tube apparatus similar to that shown in FIG. 1A-1C, having a flexible tube that has a maximum length that is limited to the length of the puller or the length of the inversion support catheter.
FIG. 2B illustrates insertion of the apparatus of claim 2A into a body lumen, though the skin.
FIG. 2C illustrate operation of the apparatus of claim 2A to remove material from the body lumen.

FIGS. 2A-2C illustrate an example of an apparatus 200 including a flexible tube that extends down the majority of the length of the inversion support catheter. In FIG. 2A, the flexible inversion support catheter 202 and flexible tube 206 are assembled with the flexible tube attached at the distal end region of the puller 204. The apparatus may be long (e.g., 50 cm or greater, 75 cm or greater, 90 cm or greater, 100 cm or greater, 110 cm or greater, 120 cm or greater, 150 cm or greater, etc.). FIGS. 2A-2C show the proximal ends of the inversion support catheter 202, which may include a hub region 212. The puller 204 is slideable within the inversion support catheter and may also include a hub 214. FIG. 2B also illustrates one example of a sheath 208 and the use of the sheath to insert the device through the skin 211 into the patient's body lumen (e.g., vessel). In FIG. 2B, the sheath (introducer sheath 208) is shown straight, but may be curved, and includes a proximal sheath hub 210. The sheath includes a lumen extending along the length. In some variations the sheath may include a valve.

In FIG. 2C, the apparatus is shown deployed (similar to FIG. 1C), with the puller retracted/retracting proximally 212 to draw the flexible tube 206 over the distal end opening of the inversion support catheter 202 and into the lumen of the inversion support catheter. This rolling and inverting movement 216 of the flexible tube may draw a material (such as a clot) into the lumen of the inversion support catheter along with the flexible tube. In FIGS. 2A-2C, the length of the flexible tube is somewhat limited by the length of the inversion support catheter. Although the flexible tube may be stretched or pulled somewhat along its length (thereby providing a slightly longer length when inside the inversion support catheter, this may be limited; the flexible tube may be configured (e.g., shape set or otherwise) to prevent it from locking down onto the outer surface of the inversion support catheter, which may otherwise increase the pull force required to drawn the flexible tube into the inversion support catheter, and therefore potentially jam or lock onto the inversion support catheter.

FIGS. 3A-3C illustrate an example of an apparatus similar to that shown in FIGS. 2A-2C, including a depot 316 for holding a compressed proximal region of the flexible tube 315. The depot may be configured to facilitate the release of the compressed flexible tube with a low release force, and in a manner that prevents snagging or binding of the flexible tube either on the body of the catheter or when rolling and inverting into the catheter. For example, FIG. 3A shows the apparatus 300 including an inversion support catheter 302, and a flexible tube 306. The flexible tube is connected to a puller 304 (optional) that may be used to draw the flexible tube over the distal end opening 309 of the inversion support catheter, as seen in FIGS. 1A-2C. Notably, while the device is illustrated in a linear form, it may be curved. Further, the examples provided herein are not shown to scale, unless otherwise indicated, although the relative relationship between the difference components may accurately reflect the interaction of the various components.

In FIG. 3A the inversion support catheter may also include a hub 312; the puller may also include a puller hub 314. Within the depot 316, the flexible tube 306 is held in a compressed form ("scrunched") so that a longitudinal section through the flexible tube forms a folded (e.g., zig-zag or fanfold pattern) in which the flexible tube is linearly compressed along the outside of the inversion support catheter, or over an inner wall of the depot (not shown). In FIG. 3A, the proximal end of the flexible tube within the depot is compressed into a folded (e.g., zig-zag or fanfold) pattern in which the flexible tube scrunched perpendicular to the inversion support catheter; e.g., the path taken by the flexible tube curves perpendicularly away and towards the long axis of the inversion support axis. In some variations these ridges of compressed flexible tube may be separated from adjacent ridges within the inner storage region 317 of the depot 316. For example, the inner storage region 317 may include channels or projections configured to separate the compressed flexible tube and to prevent it from internally snagging or catching within the depot. In some variations the flexible tube within the depot may be arranged for both packing of the flexible tube within the depot as well as to prevent snagging or locking up within the depot or leaving the depot. In any of these variations the depot may be lubricious (e.g., may include a lubricious coating, liner, etc.) and/or may be formed of a lubricous material. In particular the inner storage region of the depot may be lubricous. Alternatively, or additionally, the flexible tube may be coated with or contain a lubricous material to assist it in sliding within the apparatus.

The depot, which may be referred to herein as a proximal depot or a proximal tube depot, may be formed, at least in part, of a flexible, rigid, or semi-rigid material. In some variations the depot is configured to be rigid over at least a portion of its length, so as to prevent a user from touching the compressed flexible tube within the depot, which may result in disruption of the flexible tube and jamming of the device. For example, the depot may include ridges or struts to support the shape of the depot, even when held by the user, without collapsing or interfering with the compressed flexible tube therein. The proximal end of the depot may be configured as a depot hub 321. The depot hub may be configured to engage (e.g., releasably engage) with the inversion support catheter, e.g., the hub 312 of the inversion support catheter. The depot may be configured to slide along the outside of the inversion support catheter.

The distal end of the depot may include a distal guide 322 forming the distal end opening of the depot. The distal guide may be configured to guide the flexible tube out of the depot as the flexible tube is unfurled. For example, the distal guide may be an annular opening into the depot that may provide an outer surface that is curved towards the outer surface of the inversion support catheter. In some variations the distal guide is rigid or semi-rigid and centers and supports itself over the inversion support catheter to steer the compressed flexible tube out of the depot distally. The inner surface of the distal guide may be configured to be lubricious, to enhance release of the flexible tube.

As mentioned, the depot may generally be configured to engage with a sheath. For example, the distal guide may be configured to engage with the sheath (e.g., the sheath hub 310) in a manner that prevents snagging of the flexible tube as it leaves the inner storage region of the depot. Thus, the distal guide may be configured to engage with the introducer sheath to secure the depot to the introducer sheath. For example the depot (e.g., the distal guide of the depot) may be configured to engage over a proximal sheath hub of the introducer sheath (as will be described in FIG. 7B), and/or the depot, e.g., the distal guide portion of the depot, may be configured to engage within a proximal sheath hub of the introducer sheath. FIG. 3C shows the distal guide 322 of the depot engaging with the sheath hub 310. In FIG. 3C, the outer surface of the distal guide fits into the sheath hub. The outer surface of the distal guide region may be configured to mate (e.g., releasably mate) with the sheath hub. In some variations the distal guide is configured to fit into the sheath hub with a friction fit. In some variations the outer surface of the distal guide is configured to lock onto the sheath hub. The attachment between the distal guide and the sheath (e.g., sheath hub) may be configured to prevent a reduction in the diameter of the distal guide. In some variations the sheath may be configured so that the distal guide is configured to open to all the flexible tube to be released from the depot after engaging with the sheath. This may prevent premature release of the compressed proximal end of the flexible tube from out of the depot. In some variations one or more stays may be removed by the engagement between the distal guide and the sheath. In some variations the distal guide may be opened further once engage with the sheath, e.g., sheath hub (e.g., when engaging over and/or into the sheath hub).

For example, in FIG. 3B the apparatus of FIG. 3A is shown being inserted into the body through a sheath 308 having a sheath hub 310 at the proximal end. The apparatus may be inserted distally 311 into the body through the sheath 308. The inversion support catheter and pusher may be locked together (e.g., via the inversion support catheter hub, not shown). In some variations the depot may be locked (e.g., releasably locked) onto the inversion support catheter, e.g., at the hub 312 of the inversion support catheter. For example, in FIG. 3B, the hub of the depot 321 may be releasably engaged or locked onto the hub 312 of the inversion support catheter. Thus, the assembly may be advanced distally to the material to be removed. This process may be done under visualization (e.g., fluoroscopy) and the distal end of the apparatus may be configured to be imaged (e.g., may include radiopaque features). In some variations, as shown in FIG. 3B, the distal end of the puller may extend distally from the distal opening of the inversion support catheter, and may act (alone or in conjunction with a guidewire) to guide the apparatus to and/or against a material to be removed, such as a clot (not shown).

FIG. 3C shows the apparatus of FIGS. 3A and 3B being deployed and operated at the clot. The depot may be advanced distally 313 (e.g., over the inversion support catheter, to couple with the sheath 308, as described above. This may allow the inversion support catheter and puller to be collectively or separately advanced distally and/or retracted proximally to position the distal end of the apparatus and/or capture material from the body lumen. For example, in FIG. 3C, the puller 304 is drawn proximally 322 to invert the flexible tube 306 over and into the inversion support catheter 302 so that it rolls 316 into the distal end opening of the inversion support catheter. The inversion support catheter may be separately or concurrently advanced distally. In some variations the distal end of the depot (e.g., the depot distal guide) may be configured to receive the flexible tube from the distal opening when the depot is advanced distally over the inversion support catheter (e.g., without moving the puller proximally). Thus, the depot may be configured to receive "slack" in the flexible tube from the distal end, even while maintaining the compression of the more proximal portion of the flexible tube within the inner storage region of the depot. In some variations the distal guide of the depot may have an outwardly flared distal opening (e.g., a trumpet-shaped distal opening) that may allow the flexible tube to be guided into the distal guide from the distal end.

Figures 4A, 4B:
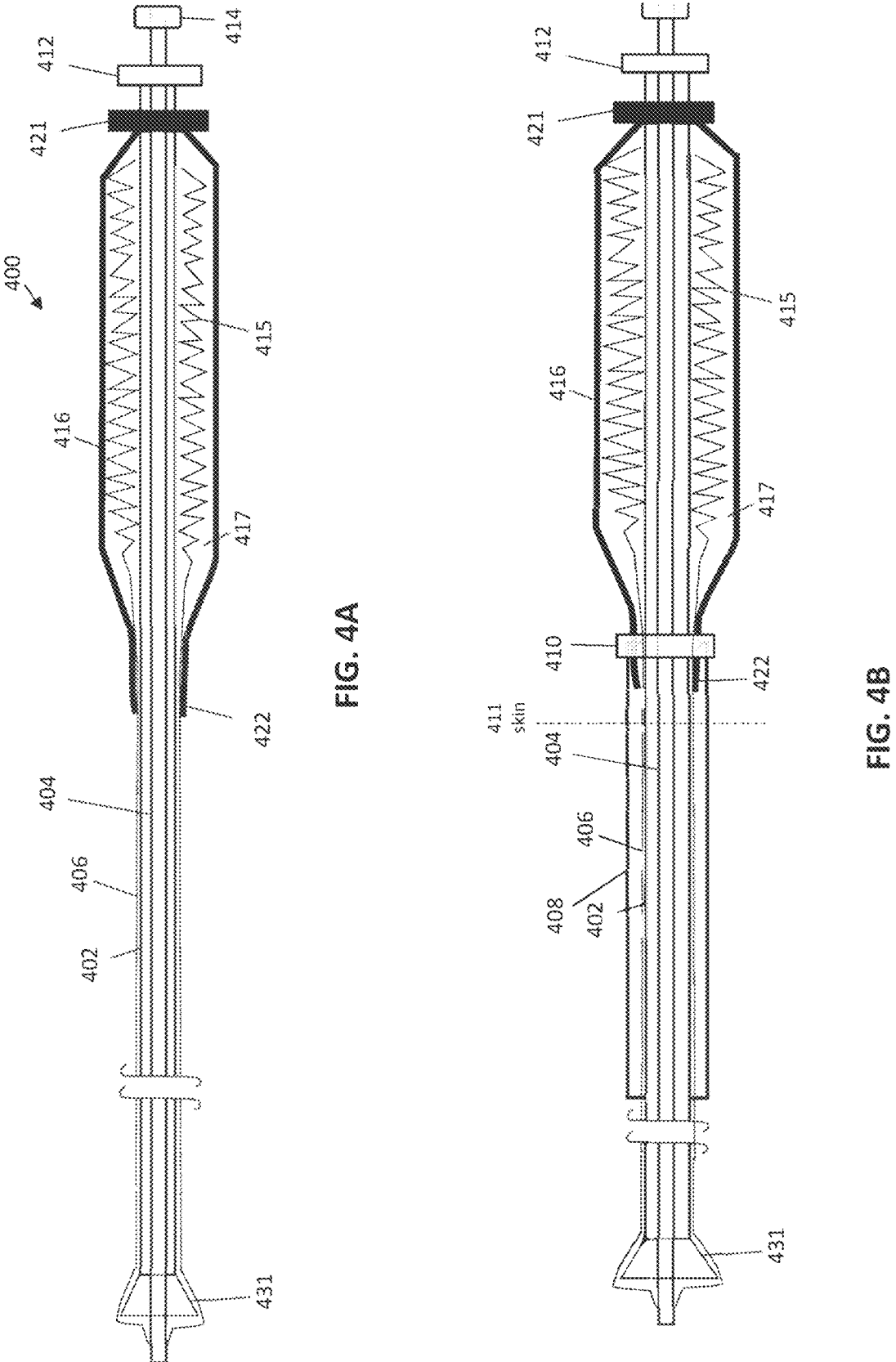
FIGS. 4A-4B illustrates another example of a mechanical inverting tube apparatus having a proximal depot configured to hold the flexible tube in a quick-release configuration.

FIGS. 4A and 4B illustrate another example of an apparatus as described herein, similar to that shown in FIGS. 3A-3C; in FIGS. 4A-4B, the distal end of the inversion support catheter is configured to have a funnel shape 431, over which the flexible tube may be pulled. Examples of this configuration may be seen, e.g., in U.S. patent application Ser. No. 16/594,256 (titled "INVERTING THROMBEC-TOMY APPARATUSES AND METHODS OF USE") filed on Oct. 7, 2019, and U.S. patent application Ser. No. 16/594,259, filed on Oct. 7, 2019.

For example, the apparatus of FIG. 4A includes an elongate inversion support catheter 402 with the funnel-shaped 431 distal end region, and a flexible tube 406 coupled to a puller 404 within the lumen of the inversion support catheter. In FIG. 4A, the proximal end of the flexible tube 415 is compressed (e.g., scrunched) within the inner storage region 417 of the depot 416. The proximal end of the sheath may include a hub 421 that may be locked or unlocked onto a hub 412 of the inversion support catheter. The puller 404 may also include a hub 414 to help in manipulating the puller and/or for releasably locking to the inversion support catheter. The depot 416 may be configured as described above, including having a distal guide 422 that may engage with a sheath, as shown in FIG. 4B.

FIG. 4B shows the apparatus 400 loaded through the sheath 408 and into a patient, through the patient's skin 411. In FIG. 4B, the apparatus is shown engaging with a sheath 408. In this example, the sheath includes a hub 410 that may engage with the distal end of the depot, as shown. For example, the distal guide 422 of the sheath may be inserted into the proximal end of the sheath; the depot may be locked onto the sheath, e.g., sheath hub.

Figures 5A, 5B, 6A, 6B:
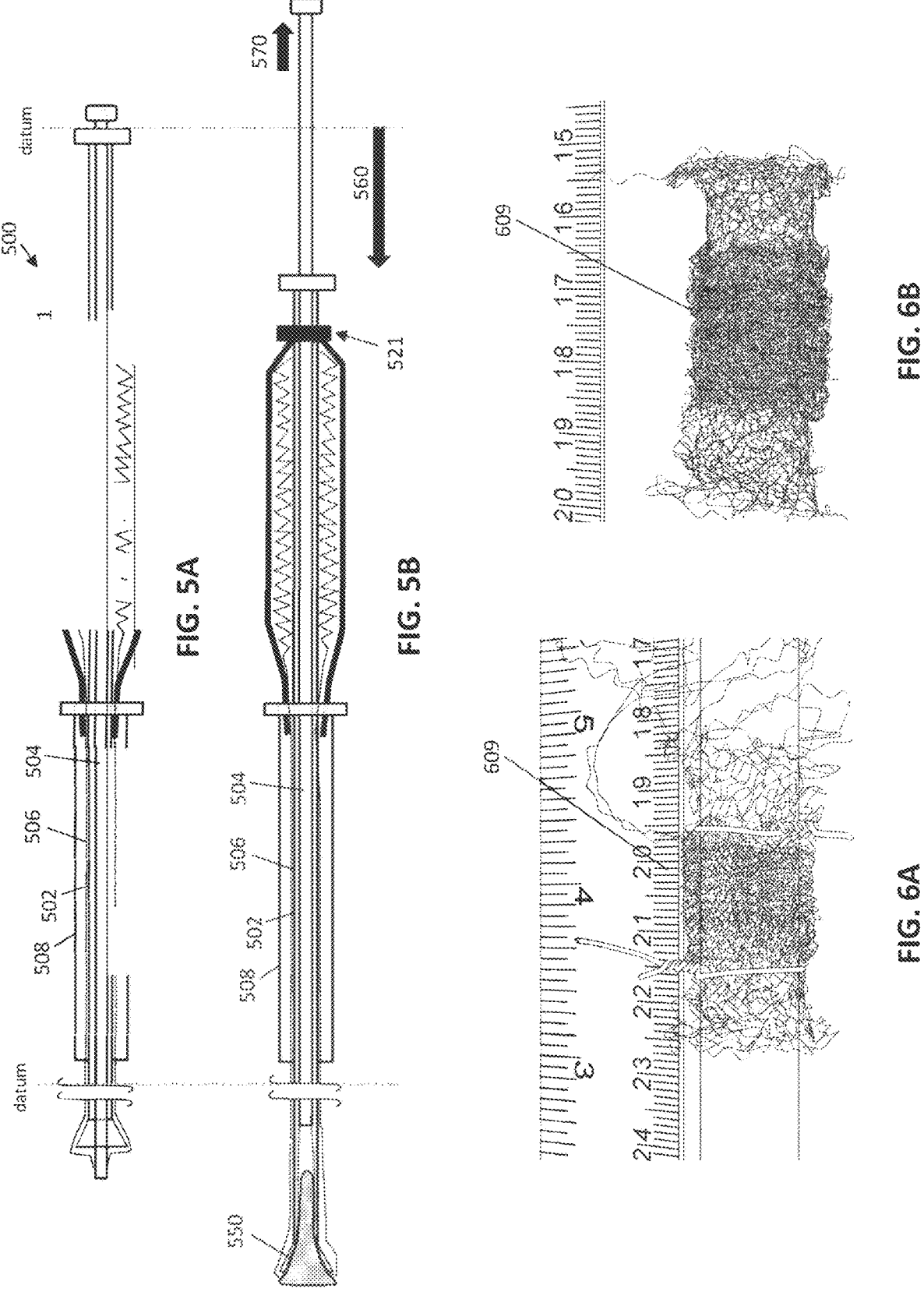
FIGS. 5A-5B illustrate an apparatus similar to that shown m FIGS. 4A-4B m operation.
FIGS. 6A-6B illustrate one example of a flexible tube (configured as a woven flexible tube) shape-set into a compressed, quick-release configuration.

FIGS. 5A-5B illustrate the operation of the apparatus shown in FIGS. 4A-4B to capture a clot material 550. As mentioned above, the thrombectomy apparatuses described herein may be advanced in the vessel by moving the sheath 508 and apparatus 500 together or relative to the sheath 508 as shown in FIGS. 5A and 5B. FIG. 5A shows a potential starting position, while FIG. 5B shows the apparatus manipulated to ingest material by advancing the inversion support catheter 502 within the sheath while optionally pulling the puller 504 proximally. In FIG. 5A the inversion support catheter 502 may be locked to the depot, e.g., by a lock (such as a locking mechanism including one or more of: a valve, a clamp, etc.) on the depot, such as the depot hub that releasably locks on to the elongate body of the inversion support catheter 502. A control (e.g., button, knob, etc.) on the depot may be used to engage/disengage the depot from the elongate inversion catheter. In FIG. 5B the depot 516 may be released from a lock and free to move relative to the elongate inversion support catheter, in this case, allowing the elongate support catheter to be advanced distally 560 as shown. The puller 504 may be pulled proximally 570 at the same time. As a result, the flexible tube 506 may be rolled over the distal end of the inversion support catheter, capturing the material 550, as shown. Any of the apparatuses describe described herein may include a lock that releasably locks the depot to the inversion support catheter.

In any of the apparatuses described herein, the flexible tube material may be compressed within the depot and secured in a compressed form. In some variations the flexible tube may be a woven tube (e.g., a plurality of woven strands) and/or a knitted tube (one or more knit strands), etc. In the examples shown, the compressed flexible tube may be compressed at a high degree of packing efficiency. For example, in FIGS. 3A-5B, the depot may hold flexible tube material at a 20 to 1 packing efficiency (e.g., a 10 cm long depot could be filled with 200 cm of scrunched flexible tube).

FIGS. 6A-6B illustrate one example of a flexible tube material 609 that is shown compressed on a mandrel from a length of 40 cm to a length of 2 cm. FIG. 6A shows the knit material that may be part of a flexible tube compressed down on a 12.5 mm mandrel; in FIG. 6B this compressed flexible tube has been annealed (e.g., via temperature setting) to retain the compressed configuration. In some variations, after forming the material (e.g., knitting, weaving, etc.) of the flexible tube, the material can then be shape set (e.g., heat set) to any radial diameter (e.g., between 1-30 cm OD). Next, the flexible tube can be loaded on a mandrel of equal or small diameter of the heat set diameter, and compressed linearly. For example, the flexible tube may be compressed axially so it randomly scrunches. Alternatively, in some variation, a compression guide may be provided to compress the flexible tube in a predictable manner. For example, a wire can first be wound around the uncompressed flexible tube on the mandrel (i.e., in a helical pattern) at a given pitch and then the flexible tube and helical wire may be compressed axially ("scrunched"), so the flexible tube is scrunched at the points the wire contacts the flexible tube. The flexible tube may then be set (e.g., heat set) in this scrunched configuration. The helical wire may be removed before, during or after enclosing in the depot. In some variations the material may be loaded into a depot in the compressed form including a compression guide (such as the helical wire describe above), with or without shape setting; the compression guide may hold the flexible tube in a compressed form. Once enclosed in the depot, which may itself hold the compressed form, the compression guide may be removed.

In some variations, before the compressed flexible tube is loaded in the depot, and to prevent snagging/catching of the flexible tube when unfurling from the depot (e.g., when pulled out of the depot guide region of the depot), in some a film, fabric or other layer of material may be included on or in the flexible tube (including the helical wire discussed above), such as on the outside or inside of the flexible tube, that may act like a release, preventing two adjacent compressed regions (e.g., peaks of the fanfold and/or zig-zag shaped flexible tube) from contacting each other within the depot.

In some variations the apparatus may be configured so that the flexible tube is modified after it is compressed, e.g., by twisting, rotating, turning, etc. to further compress and/or to load into the depot. For example, in some variations the compressed (e.g., scrunched) flexible tube is twisted along its length (e.g., clockwise and/or counterclockwise) on the inversion support catheter, or a mandrel, prior to being enclosed in the inner storage region of the depot. Thus, in some variations the flexible tube within the depot is compressed as described herein and may be further twisted.

Any of the flexible tubes described herein may not be shape-set into the compressed configuration. For example, the flexible tube may be heat set to the radius of or slightly larger than the inversion support catheter in the un-inverted (and in some variations an inverted radius may be set, as described above), in a straight/uncompressed configuration, and then compressed and held in the depot. This may reduce the friction will pulling knit out of the depot.

Figure 7A:
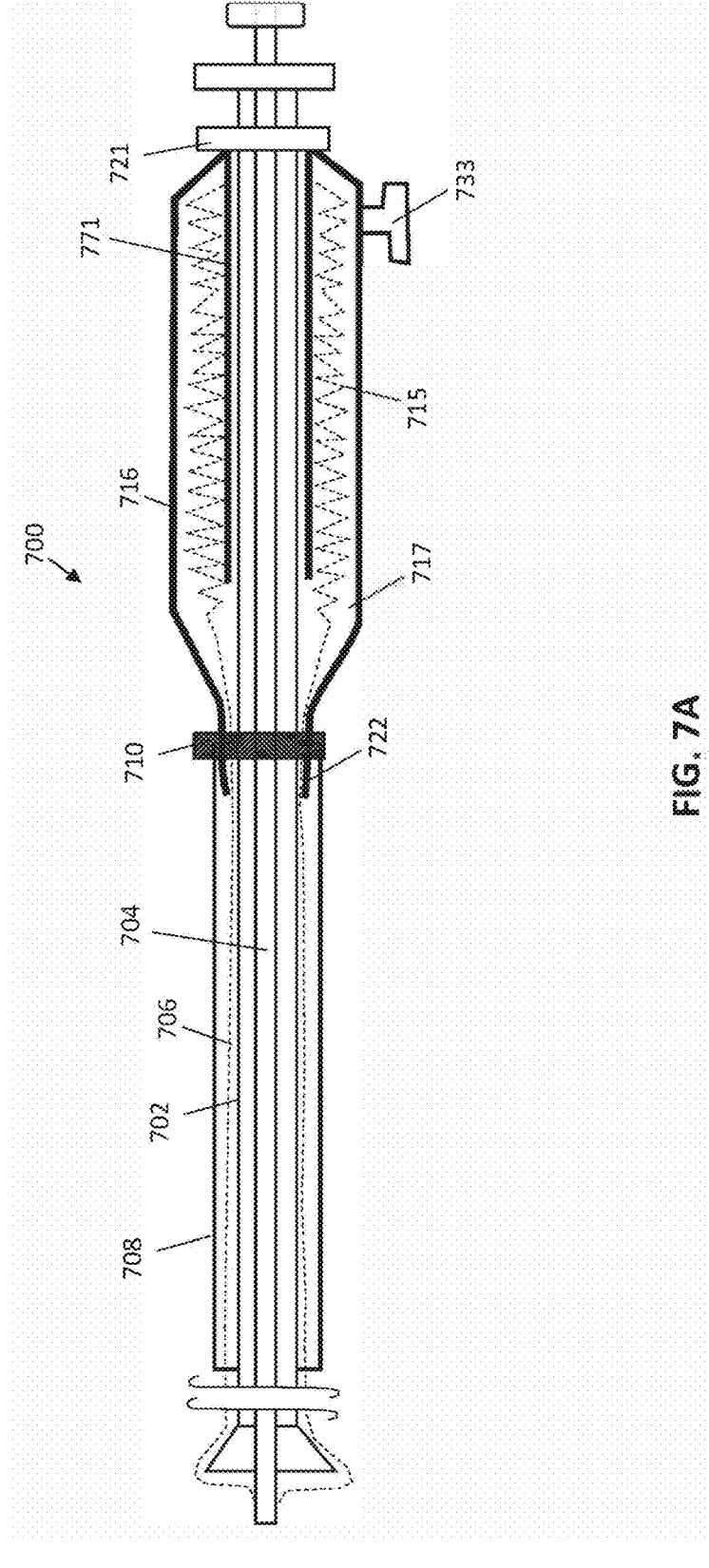
FIG. 7A illustrate another example of a mechanical inverting tube apparatus having a depot, including an inner liner and a valve for flushing and/or pressurizing the depot.

FIG. 7A illustrates one example of an apparatus 700 as described herein, similar to that shown above, in which the depot 716 includes an inner lining 771 within the inner storage region 707. The inner lining may extend over and around the inversion support catheter, and may be rigid or semi-rigid. This inner lining may also be lubricous.

The depot 716 in FIG. 7A also includes a flushing valve 733 that may be used, for example, for connection to a fluid (e.g., saline) for flushing the depot during or before use. In some variations the depot includes a hub 721 that may engage with the inversion support catheter 702. The sheath 708 (including sheath hub 710) may be configured to engage with the depot (e.g., a distal guide 722 of the depot). In some variations this may be a locking engagement (e.g., a releasable locking engagement). This engagement may be water or pressure-tight (e.g., the depot and the sheath may be sealingly engaged). In any of the variations described herein the depot may be pressurized (e.g., by including a pressurized fluid, which may help unfurl the flexible tube 706 when it is pulled distally out of the depot, e.g., by pulling on the puller 704. In some variations a saline may be injected via the port 733; in some variations, a contrast agent may be introduced through the depot via the same or a different port. Alternatively, or additionally, a lubricant may be injected through the depot. As mentioned, the depot can be pressurized with saline or other fluids to produce a positive pressure, which may reduce or stop retrograde patient blood flow into the depot.

Figure 7B:
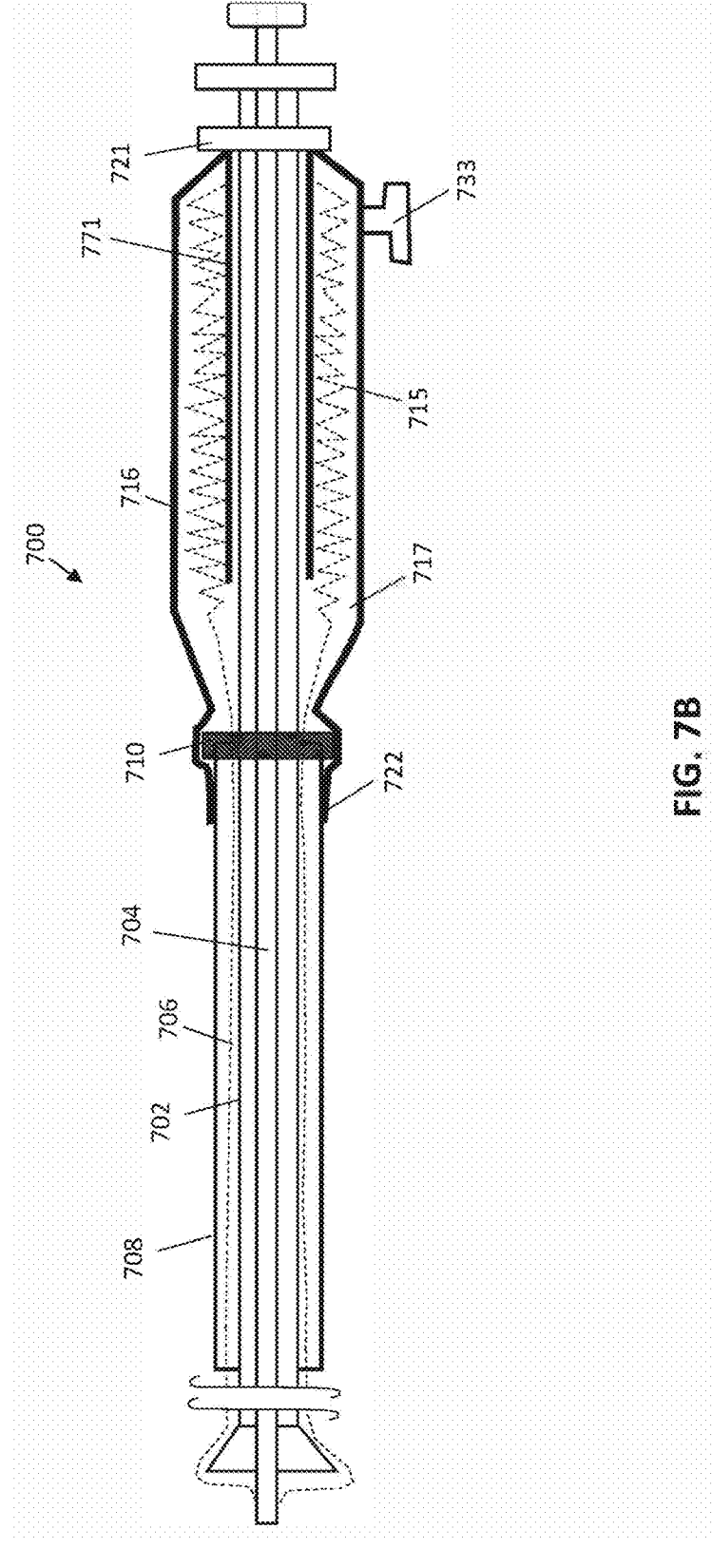
FIG. 7B is an example of a mechanical inverting tube apparatus having a depot configured to attach over in sheath.

In FIG. 7A the distal guide 722 of the depot 716 engages with the sheath 708 by inserting into the sheath. FIG. 7B illustrates an example in which the distal end 722 of the depot 716 engages with the sheath 708 by attaching over the sheath. Coupling the depot to the sheath over the sheath may reduce any potential pinch points as the flexible tube unfurls through the sheath. The depot to sheath junction may be sealed in some configurations.

As mentioned above, the flexible tube may be any appropriate material, such as a knit, a weave, a braid, or a non-woven material (both solid and/or laser slotted). In some variations the flexible tube comprises a metallic material, a polymeric material, and/or mixes of the two. In general, to reduce the friction in the system as the weave is unfurled out of the depot and through the sheath, the depot can be made from a slippery material such as PTFE, PE, hard polymer. Alternatively, or additionally, the weave can be coated with a lubricious coating, and/or the depot inner chamber can be coated with a lubricious coating.

Figures 8A, 8B:
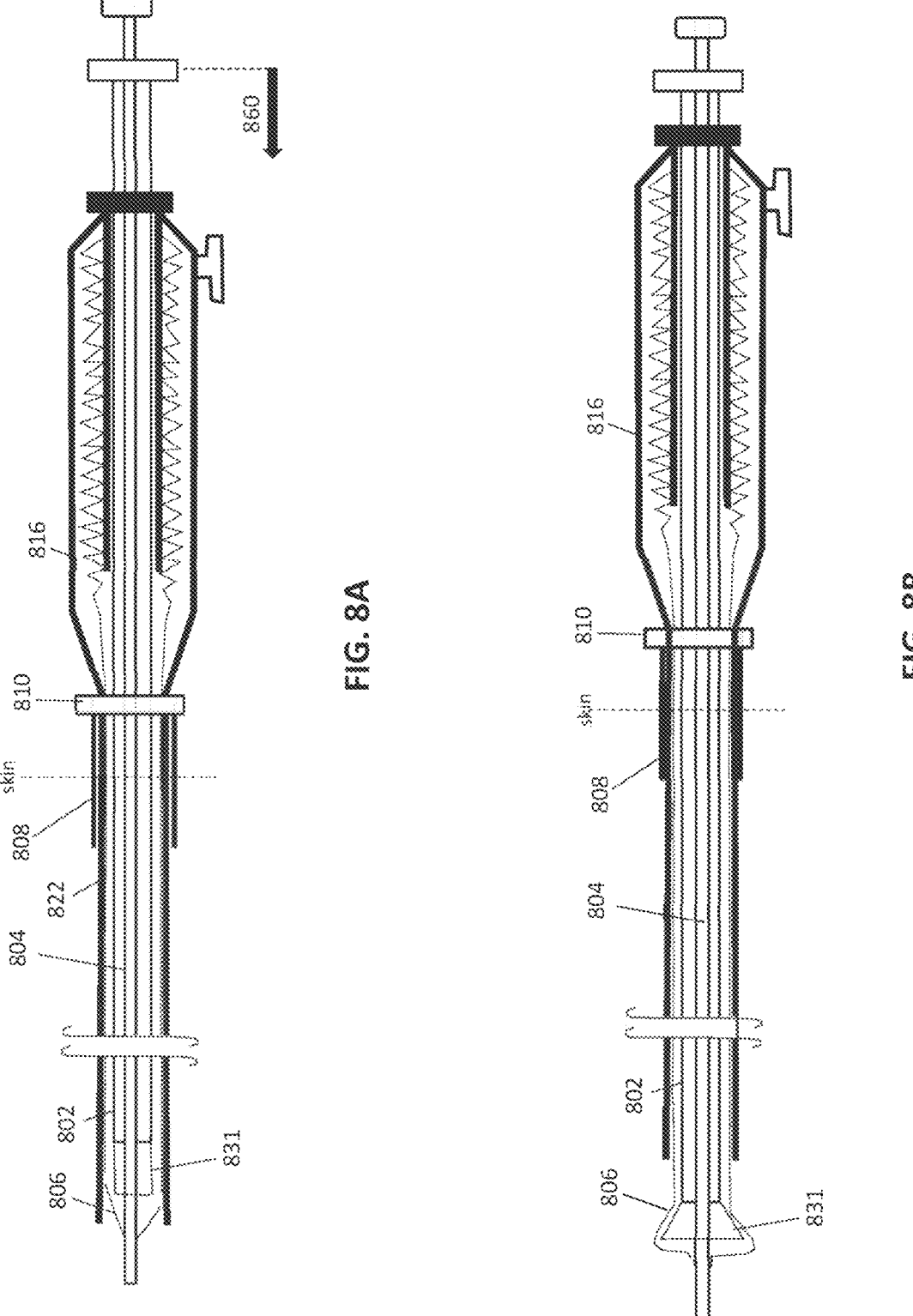
FIGS. 8A-8B illustrate another example of a mechanical inverting tube apparatus having a depot, in which the depot includes a distal sleeve portion.

In general, the length of the distal end (e.g., distal guide) of the depot can be any length, and may be funnel-shaped or tapered at either or both ends. In some variations the distal end of the depot can be made from PTFE or lubricious coating. For example, FIGS. 8A and 8B illustrate two examples of apparatuses including depots having distal guide regions that are longer. The longer distal guide regions may help maintain the compressed form of the flexible tube and may protect and constrain the flexible tube along much of the length of the inversion support catheter, as shown. For example, in FIG. 8A, the apparatus 800 includes an inversion support catheter 802, and a flexible tube 806 coupled to a distal end region of a puller 804. The apparatus is inserted through the sleeve 808 into the body. In this example the distal guide region 822 of the depot 816 extends much further than the introducer sheath 810. Although FIGS. 8A and 8B show the distal guide region extending down much of the length of the inversion support catheter, in some variations, the distal guide region extends between 85% and 20% the length of the inversion support catheter (e.g., 90% or less, 85% or less, 80% or less, 75% or less, 70% or less, 65% or less, 60% or less, 55% or less, 50% or less, 45% or less, etc.). In FIG. 8A, the apparatus is undeployed; FIG. 8B shows the apparatus of FIG. 8A in a deployed configuration, by driving the inversion support catheter distally 860 and/or pulling the puller 804 proximally. The short introducer sheath 808 may include a proximal end (e.g., proximal hub 810) that engages with the depot 816. In FIG. 8B, the distal end of the apparatus is inserted through the sheath to clot face, and the distal funnel region 831 may be extended and expanded outwards.

In any of the variations described herein, the proximal end of the sheath, e.g., outside of the patient, may be larger in diameter than more distal regions in order to remove pinch point and connect to a wider mouth depot connection junction point. In some variations the sheath may have a wider mouth with a funnel taper to make the flexible tube deploy with less friction into a smaller sheath ID inside the patient.

Figure 9:
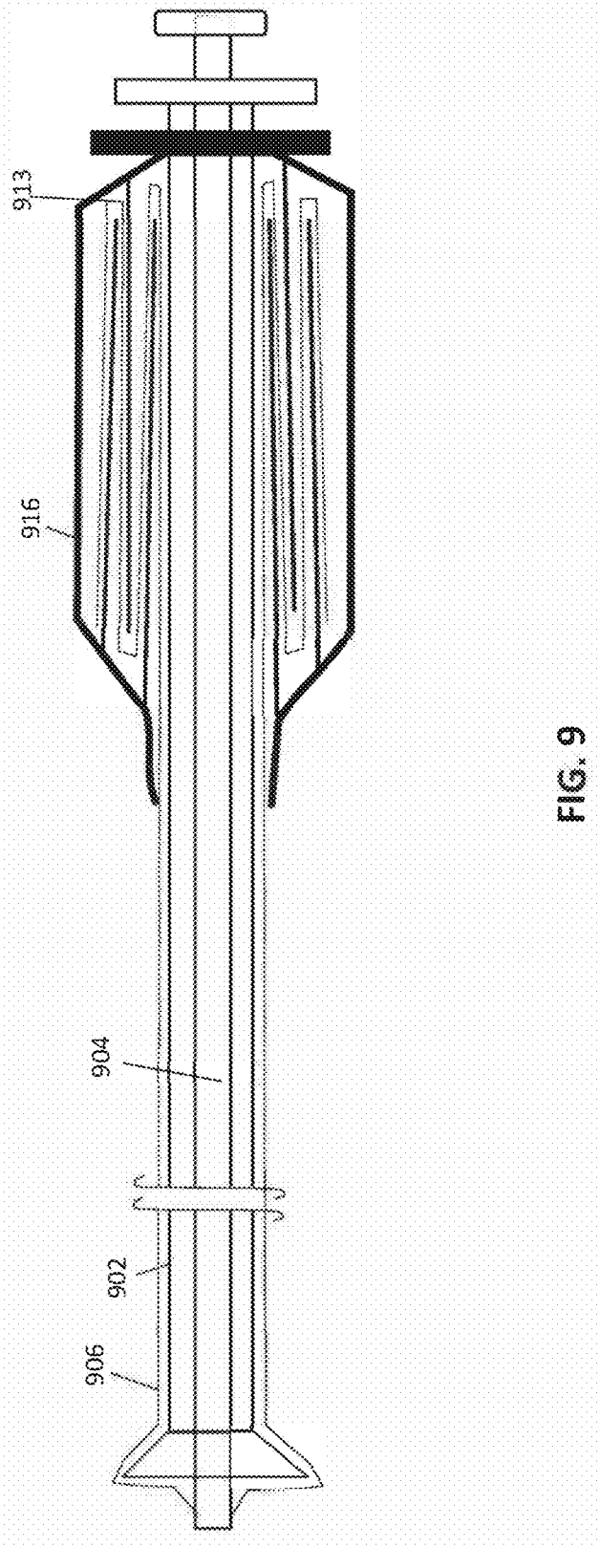
FIG. 9 shows another example of a mechanical inverting tube apparatus having a depot including guides for guiding the flexible tube.

Although the majority of the examples described above include the flexible tube compressed linearly within the depot, in some variations the flexible tube may be compressed in one or more alternative ways. For example, in FIG. 9 the depot 916 includes a layered structure within the inner storage region of the depot, which is divided up into multiple layers 913 to hold the flexible tube 906. The device also includes an inversion support catheter 902 and a puller 904 as described above.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. An apparatus for removing a material from a body lumen, the apparatus comprising:
an elongate inversion support catheter having a proximal end region, a distal end region, and a distal end opening;
an elongate puller extending within the inversion support catheter;
a flexible tube having a distal first end attached to the puller, wherein the flexible tube extends over an outer surface of the inversion support catheter and is configured to invert into the distal end opening of the inversion support catheter when the puller is pulled proximally; and
a depot movably coupled to the proximal end region of the inversion support catheter, the depot comprising an inner storage region, wherein a proximal portion of the flexible tube is held compressed within the inner storage region in a folded configuration that is configured to unfurl out of a distal end opening of the depot, move distally from the depot along the outer surface of the inversion support catheter, and invert into the distal opening of the inversion support catheter when the puller is pulled proximally within the inversion support catheter.

2. The apparatus of claim 1, further comprising a distal guide forming the distal end opening of the depot, wherein the distal guide is configured to guide the flexible tube out of the depot as the flexible tube is unfurled.

3. The apparatus of claim 2, further comprising an introducer sheath, wherein the distal guide is configured to engage with the introducer sheath to secure the depot to the introducer sheath.

4. The apparatus of claim 3, wherein the depot is configured to engage over a proximal sheath hub of the introducer sheath.

5. The apparatus of claim 3, wherein the depot is configured to engage within a proximal sheath hub of the introducer sheath.

6. The apparatus of claim 1, wherein the depot comprises a transparent outer region allowing visualization of the flexible tube within the inner storage region.

7. The apparatus of claim 1, wherein in the folded configuration, the flexible tube comprises a zig-zag pattern that is disposed in parallel to a long axis of the inversion support catheter.

8. The apparatus of claim 1, wherein in the folded configuration, the flexible tube comprises a zig-zag pattern of the flexible tube that is disposed transverse to a long axis of the inversion support catheter.

9. The apparatus of claim 1, wherein greater than 50% of a length of the flexible tube is held within the depot in an undeployed configuration.

10. The apparatus of claim 1, wherein the flexible tube is held compressed within the inner storage region with greater than a 10-fold compression along the length of the flexible tube.

11. The apparatus of claim 1, further comprising a valve on the depot configured to receive a flushing solution and/or a pressurizing solution.

12. The apparatus of claim 1, wherein the depot is slidable along the inversion support catheter.

13. An apparatus for removing a material from a body lumen, the apparatus comprising:
an elongate inversion support catheter having a proximal end region, a distal end region, and a distal end opening;
an elongate puller extending within the inversion support catheter;
a flexible tube having a distal first end attached to the puller, wherein the flexible tube extends over an outer surface of the inversion support catheter and is configured to invert into the distal end opening of the inversion support catheter when the puller is pulled proximally;
a depot slidably coupled to the proximal end region of the inversion support catheter, the depot comprising an inner storage region, wherein a proximal portion of the flexible tube is held compressed within the inner storage region in a fanfold configuration, and is configured to unfurl out of a distal end opening of the depot, move distally from the depot along the outer surface of the inversion support catheter, and invert into the distal opening of the inversion support catheter when the puller is pulled proximally within the inversion support catheter; and a distal guide forming the distal end opening of the depot, wherein the distal guide is configured to engage with an introducer sheath, and to guide the flexible tube out of the depot as the flexible tube is unfurled.

14. A method of removing a clot from a blood vessel, the method comprising:

advancing an inverting tube apparatus through the blood vessel until a distal end portion of the inverting tube apparatus is located proximate to the clot, wherein the inverting tube apparatus comprises an inversion support catheter having an elongate and flexible catheter body, a puller within a lumen of the inversion support catheter, and a flexible tube coupled at a distal end to the puller, the flexible tube extending over an exterior surface of the inversion support catheter, wherein the flexible tube is held compressed within an inner storage region of a depot on a proximal end region of the inversion support catheter;

pulling the puller proximally to thereby roll the flexible tube over a distal end opening of the inversion support catheter so that the flexible tube captures the clot and pulls the clot proximally into the lumen of the inversion support catheter;

wherein pulling the puller proximally draws the flexible tube from out of the depot so that the flexible tube unfurls distally from a compressed fanfold configuration within the depot and moves distally from the depot along the outer surface of the inversion support catheter.

15. The method of claim 14, wherein pulling the puller proximally to draw the flexible tube from out of the depot comprises guiding the flexible tube out of the inner storage region using a distal guide on the depot.

16. The method of claim 14, further comprising inserting the inverting tube apparatus into an introducer sheath and into the blood vessel.

17. The method of claim 16, further comprising locking the depot to a proximal end of the introducer sheath.

18. The method of claim 14, further comprising pressurizing the inner storage region of the depot.

19. The method of claim 14, further comprising flushing a flushing fluid through the depot.

20. The method of claim 14, further comprising injecting a contrast agent through the depot.

* * * * *